US011951162B2

(12) United States Patent
Kim et al.

(10) Patent No.: US 11,951,162 B2
(45) Date of Patent: Apr. 9, 2024

(54) STREPTOCOCCUS PNEUMONIAE CAPSULAR POLYSACCHARIDES AND IMMUNOGENIC CONJUGATE THEREOF

(71) Applicant: SK BIOSCIENCE CO., LTD., Seongnam-si (KR)

(72) Inventors: Hun Kim, Suwon-si (KR); Dong Soo Ham, Suwon-si (KR); Jin-Hwan Shin, Seoul (KR); Kyung-jun An, Seoul (KR); Sung-hyun Kim, Yongin-si (KR)

(73) Assignee: SK BIOSCIENCE CO., LTD., Seongnam-si (KR)

( * ) Notice: Subject to any disclaimer, the term of this patent is extended or adjusted under 35 U.S.C. 154(b) by 25 days.

(21) Appl. No.: 17/047,563

(22) PCT Filed: Apr. 18, 2019

(86) PCT No.: PCT/KR2019/004717
§ 371 (c)(1),
(2) Date: Oct. 14, 2020

(87) PCT Pub. No.: WO2019/203599
PCT Pub. Date: Oct. 24, 2019

(65) Prior Publication Data
US 2021/0154287 A1 May 27, 2021

(30) Foreign Application Priority Data

Apr. 18, 2018 (KR) .................. 10-2018-0045245
Apr. 18, 2018 (KR) .................. 10-2018-0045246
Apr. 18, 2018 (KR) .................. 10-2018-0045247
Apr. 18, 2018 (KR) .................. 10-2018-0045248

(51) Int. Cl.
*A61K 39/09* (2006.01)
*A61K 47/61* (2017.01)
*C07K 14/315* (2006.01)

(52) U.S. Cl.
CPC .......... *A61K 39/092* (2013.01); *A61K 47/61* (2017.08); *C07K 14/315* (2013.01)

(58) Field of Classification Search
None
See application file for complete search history.

(56) References Cited

U.S. PATENT DOCUMENTS

| | | | | |
|---|---|---|---|---|
| 5,153,312 A | * | 10/1992 | Porro | .................. A61K 39/092 530/410 |
| 5,773,007 A | | 6/1998 | Penney et al. | |
| 6,132,723 A | | 10/2000 | Malcolm | |
| 6,168,796 B1 | | 1/2001 | Malcolm | |
| 7,955,605 B2 | * | 6/2011 | Prasad | .................... A61P 31/04 424/244.1 |
| 8,029,798 B2 | * | 10/2011 | Leroy | .................. A61K 39/092 424/197.11 |
| 11,123,417 B2 | * | 9/2021 | An | ....................... A61K 39/092 |
| 11,147,864 B2 | * | 10/2021 | An | ..................... A61K 47/6415 |
| 11,224,652 B2 | | 1/2022 | An et al. | |
| 11,241,489 B2 | | 2/2022 | An et al. | |
| 2003/0099672 A1 | | 5/2003 | Schultz | |
| 2005/0009121 A1 | | 1/2005 | Talaga et al. | |
| 2011/0117123 A1 | | 5/2011 | Leroy | |
| 2011/0195086 A1 | | 8/2011 | Caulfield et al. | |
| 2011/0212124 A1 | | 9/2011 | Boutriau et al. | |
| 2012/0052088 A1 | | 3/2012 | Davis et al. | |
| 2012/0328659 A1 | | 12/2012 | Denoel et al. | |
| 2013/0072881 A1 | | 3/2013 | Lakshmi et al. | |
| 2013/0266609 A1 | | 10/2013 | Boutriau | |
| 2014/0099337 A1 | | 4/2014 | Davis et al. | |
| 2014/0322263 A1 | | 10/2014 | Siber et al. | |
| 2015/0190520 A1 | | 7/2015 | Shin et al. | |
| 2015/0202309 A1 | | 7/2015 | Emini et al. | |
| 2015/0265702 A1 | | 9/2015 | Biemans et al. | |
| 2015/0343076 A1 | | 12/2015 | Park et al. | |
| 2017/0157241 A1 | | 6/2017 | Li | |
| 2018/0000922 A1 | | 1/2018 | Cooper et al. | |
| 2019/0192648 A1 | | 6/2019 | Smith et al. | |
| 2020/0230233 A1 | | 7/2020 | An et al. | |
| 2020/0237889 A1 | | 7/2020 | An et al. | |
| 2020/0360502 A1 | | 11/2020 | An et al. | |
| 2021/0077608 A1 | | 3/2021 | An et al. | |
| 2021/0283247 A1 | | 9/2021 | Hausdorff et al. | |
| 2021/0401963 A1 | | 12/2021 | An et al. | |
| 2022/0031828 A1 | | 2/2022 | An et al. | |

FOREIGN PATENT DOCUMENTS

AU 2007200116 A1 1/2007
AU 2010235979 A1 11/2010
(Continued)

OTHER PUBLICATIONS

Google translation of WO 2013/191459.*
Yano et al., "Characterization of Gene Use and Efficacy of Mouse Monoclonal Antibodies to *Streptococcus pneumoniae* Serotype 8", Clinical and Vaccine Immunology, 2011, vol. 18, No. 1, pp. 59-66.
Buchwald et al., "A Peptide Mimotope of Type 8 PneumococcaCapsular Polysaccharide Induces a Protective Immune Response in Mice", Infection and Immunity, 2005, vol. 73, No. 1, pp. 325-333.

(Continued)

*Primary Examiner* — Oluwatosin A Ogunbiyi
(74) *Attorney, Agent, or Firm* — MH2 TECHNOLOGY LAW GROUP, LLP

(57) ABSTRACT

The present invention provides an immunogenic composition comprising a *Streptococcus pneumoniae* polysaccharide-protein conjugate, comprising a capsular polysaccharide derived from one or more selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and one or 2 or more of carrier proteins conjugated to the respective capsular polysaccharide, and method of preparation thereof. Through one example of the present invention, an immunogenic composition for preventing or treating pneumococcal infection can be provided.

16 Claims, No Drawings

(56) References Cited

FOREIGN PATENT DOCUMENTS

| | | |
|---|---|---|
| CA | 2153730 A1 | 1/1997 |
| CA | 2153733 A1 | 1/1997 |
| CN | 1060408 A | 4/1992 |
| CN | 1255861 A | 6/2000 |
| CN | 101180079 A | 5/2008 |
| CN | 101785857 A | 7/2010 |
| CN | 101818185 A | 9/2010 |
| CN | 102068690 A | 5/2011 |
| CN | 102858365 A | 1/2013 |
| CN | 103599529 A | 2/2014 |
| CN | 103656631 A | 3/2014 |
| CN | 103656632 A | 3/2014 |
| CN | 107029225 A | 8/2017 |
| EP | 2932979 A1 | 10/2015 |
| IN | 201917040656 | 8/2019 |
| KR | 10-2012-0005537 A | 1/2012 |
| KR | 10-2013-0142574 A | 12/2013 |
| KR | 10-2014-0075201 A | 6/2014 |
| KR | 10-2016-0098507 A | 8/2016 |
| KR | 10-2017-0016360 A | 2/2017 |
| KR | 10-1730749 B1 | 4/2017 |
| KR | 10-2017-0102009 A | 9/2017 |
| KR | 10-2018-0027353 A | 3/2018 |
| KR | 10-2018-0105590 A | 9/2018 |
| TW | 201008577 A | 3/2010 |
| TW | I341210 B | 5/2011 |
| WO | 96/40225 A1 | 12/1996 |
| WO | 9851339 A1 | 11/1998 |
| WO | 00/56359 A2 | 9/2000 |
| WO | 02/00249 A2 | 1/2002 |
| WO | 02/080965 A2 | 10/2002 |
| WO | WO 03/051392 * | 6/2003 |
| WO | 2006/032499 A1 | 3/2006 |
| WO | 2008/079732 A2 | 7/2008 |
| WO | 2009/000824 A2 | 12/2008 |
| WO | 2009/000826 A1 | 12/2008 |
| WO | 2009000825 A2 | 12/2008 |
| WO | 2010/125480 A1 | 11/2010 |
| WO | 2011/100151 A1 | 8/2011 |
| WO | 2013/191459 A1 | 12/2013 |
| WO | 2014/027302 A1 | 2/2014 |
| WO | 2014/092377 A1 | 6/2014 |
| WO | 2014/118201 A1 | 8/2014 |
| WO | 2015/110940 A2 | 7/2015 |
| WO | 2015/110941 A2 | 7/2015 |
| WO | 2015/110942 A2 | 7/2015 |
| WO | WO 2015/175355 * | 11/2015 |
| WO | 2016/207905 A2 | 12/2016 |
| WO | 2017/067962 A1 | 4/2017 |
| WO | 2017/085586 A1 | 5/2017 |
| WO | 2017/173415 A2 | 10/2017 |
| WO | 2018/027123 A1 | 2/2018 |
| WO | 2018/027126 A1 | 2/2018 |
| WO | 2018/064444 A1 | 4/2018 |
| WO | 2019/050813 A1 | 3/2019 |
| WO | 2019/050815 A1 | 3/2019 |
| WO | 2019/050816 A1 | 3/2019 |
| WO | 2019/050818 A1 | 3/2019 |
| WO | 2019/070994 A1 | 4/2019 |
| WO | 2019/152921 A1 | 8/2019 |
| WO | 2019/152925 A1 | 8/2019 |
| WO | 2021/021729 A1 | 2/2021 |

OTHER PUBLICATIONS

Malcolm et al., "Chapter 21: Surface Layers from Bacillus Alvei as a Carrier for a *Streptococcus pneumoniae* Conjugate Vaccine", In: Beveridge T.J., Koval S.F. (eds) Advances in Bacterial Paracrystalline Surface Layers. NATO ASI Series (Series A: Life Sciences), 1993, vol. 252, pp. 219-233.

Malcolm et al., "Chapter 13: Crystalline Bacterial Cell Surface Layers (S-Layers) as Combined Carrier/Adjuvants for Conjugate Vaccines", In: Sleytr U.B., Messner P., Pum D., Sara M. (eds) Immobilised Macromolecules: Application Potentials. Springer Series in Applied Biology. Springer, London, 1993, pp. 195-207.

Malcolm et al., "S30: Improved Immunogenicity Using OligosaccharideConjugate Vaccines", Glyco XIII: XIIIth International Symposium on Glycoconjugates; Seattle, USA, Aug. 20-26, 1995, Glycoconjugate Journal, 1995, vol. 12, p. 560.

Jahn-Schmid et al., "Toward selective elicitation of TH1-controlled vaccination responses: vaccine applications of bacterial surface layer proteins", Journal of Biotechnology, 1996, vol. 44, pp. 225-231.

Thanos et al., "Invasive Infektion durch *Streptococcus pneumoniae* Serotyp 8 im Säuglingsalter", Monatsschr Kinderheilkd, 2013, vol. 161, pp. 1177-1179, with English abstract.

Office Action dated Aug. 10, 2020 for U.S. Appl. No. 16/322,698, 23 pages.

Office Action dated Mar. 25, 2021 for U.S. Appl. No. 16/322,698, 13 pages.

Office Action dated Mar. 15, 2021 for U.S. Appl. No. 16/322,726, 21 pages.

International Search Report dated Jul. 16, 2019 for International Patent Application No. PCT/KR2019/004717, 20 pages with English translation.

Bethell et al., "A Novel Method of Activation of Cross-linked Agaroses with 1,1'-Carbonyldiimidazole Which Gives a Matrix for Affinity Chromatography Devoid of Additional Charged Groups", The Journal of Biological Chemistry, 1979, vol. 245, No. 8, pp. 2572-2574.

Extended European Search Report dated Mar. 18, 2022 for European Patent Application No. 19748037.9, 12 pages.

Extended European Search Report dated Mar. 18, 2022 for European Patent Application No. 19747393.7, 12 pages.

Anderson et al., "Non-interference between two protein carriers when used with the same polysaccharide for Pneumococcal conjugate vaccines in 2-year-old children," Vaccine, 2003, vol. 21, No. 13-14, pp. 1554-1559.

Sigurdardottir et al., "Immune response to octavalent diphtheria- and tetanus-conjugated Pneumococcal vaccines is serotype- and carrier-specific: the choice for a mixed carrier vaccine," The Pediatric Infectious Disease Journal, 2002, vol. 21, No. 6, pp. 548-554.

Wuorimaa et al., "Tolerability and immunogenicity of an eleven-valent Pneumococcal conjugate vaccine in healthy toddlers, " The Pediatric Infectious Disease Journal, 2001, vol. 20, No. 3, pp. 272-277.

Extended European Search Report dated Mar. 16, 2022 for European Patent Application No. 19788873.8, 14 pages.

International Search Report and Written Opinion dated Oct. 24, 2017 from International Application No. PCT/US2017/045483 (Authorized Officer, Blaine R. Copenheaver), 10 Pages.

Durando et al., "Experience with *Pneumococcal polysaccharide* conjugate vaccine (conjugated to CRM197 carrier protein) in children and adults", Clinical Microbiology Infection, Oct. 1, 2013, vol. 19, Suppl. 1, pp. 1-9.

Daniels et al., "A Review of Pneumococcal Vaccines: Current Polysaccharide Vaccine Recommendations and Future Protein Antigens", J Pediatr Pharmacol Ther, 2016, vol. 21, No. 1, pp. 27-35.

International Search Report and Written Opinion dated Oct. 30, 2017 from International Application No. PCT/US2017/045479 (Authorized Officer, Shane Thomas), 9 Pages.

Jakobsen et al., "Intranasal Immunization with Pneumococcal Polysaccharide Conjugate Vaccines Protects Mice against Invasive Pneumococcal Infections", Infection and Immunity, Aug. 1999, vol. 67, No. 8, pp. 4128-4133.

Prymula et al., "Pneumococcal capsular polysaccharides conjugated to protein D for prevention of acute otitis media caused by both *Streptococcus pneumoniae* and non-typable Haemophilus influenzae: a randomised double-blind efficacy study", Lancet, 2006, vol. 367, pp. 740-748.

Dagan et al., "Reduction of Antibody Response to an 11-Valent Pneumococcal Vaccine Coadministered with a Vaccine Containing Acellular Pertussis Components", Infection and Immunity, September 20014, vol. 72, No. 9, pp. 5383-5391.

Fattom et al., "Serum Antibody Response in Adult Volunteers Elicited by Injection of Streptococcus pneumoniae Type 12F Poly-

(56) References Cited

OTHER PUBLICATIONS saccharide Alone or Conjugated to Diphtheria Toxoid", Infection and Immunity, Jul. 1990, vol. 58, No. 7, pp. 2309-2312.
Andrews et al., "Serotype-specific effectiveness and correlates of protection for the 13-valent pneumococcal conjugate vaccine: a postlicensure indirect cohort study", Lancet Infect Dis, Jul. 18, 2014, 8 pages.
Juergens et al., "Post Hoc Analysis of a Randomized Double-Blind Trial of the Correlation of Functional and Binding Antibody Responses Elicited by 13-Valent and 7-Valent Pneumococcal Conjugate Vaccines and Association with Nasopharyngeal Colonization", Clinical and Vaccine Immunology, Sep. 2014, vol. 21, No. 9, pp. 1277-1281.
Nurkka et al., "Serum and salivary anti-capsular antibodies in infants and children vaccinated with octavalent pneumococcal conjugate vaccines, PncD and PncT", Vaccine, 2002, vol. 20, pp. 194-201.
Pfizer, "PREVNAR 13 (Pneumococcal 13-valent Conjugate Vaccine [Diphtheria CRM197 Protein]) Suspension for Intramuscular injection", Prevnar 13 Full Prescribing Information, 2010, 47 pages.
Vesikari et al., "Immunogenicity of the 10-Valent Pneumococcal Non-typeable Haemophilus influenzae Protein D Conjugate Vaccine (PHiD-CV) Compared to the Licensed 7vCRM Vaccine", The Pediatric Infectious Disease Journal, Apr. 2009, vol. 28, No. 4, Supplement pp. S66-S76.
Wuorimaa et al., "Tolerability and immunogenicity of an 11-valent pneumococcal conjugate vaccine in adults", Vaccine, 2001, vol. 19, pp. 1863-1869.
International Search Report and Written Opinion dated Apr. 15, 2019 from International Application No. PCT/US2019/016506 (Authorized Officer, Shane Thomas), 11 Pages.
Extended European Search Report dated Mar. 10, 2020 for European Patent Application No. 17837752.9, 12 pages.
Dagan et al., "Tolerability and immunogenicity of an eleven valent mixed carrier Streptococcus pneumoniae capsular polysaccharide-diphtheria toxoid or tetanus protein conjugate vaccine in Finnish and Israeli infants", The Pediatric Infectious Disease Journal, Feb. 2004, vol. 23, No. 2, pp. 91-98.
International Search Report and Written Opinion dated Jul. 1, 2019 from International Application No. PCT/US2019/016511 (Authorized Officer, Lee W. Young), 9 pages.
Martens et al., "Serotype-specific mortality from invasive *Streptococcus pneumoniae* disease revisited", BMC Infectious Diseases, 2004, vol. 4, No. 21, 7 pages.
Sanofi's Opposition To Pfizer's Motion to Amend dated Nov. 16, 2018 from IPR Trial No. IPR2018-00187 for U.S. Pat. No. 9,492,559 (*Sanofi Pasteur Inc. and SK Chemicals Co., Ltd.* vs. *Pfizer, Inc.*), 42 pages.
Loek Van Alphen, "Exhibit 1101, Declaration of Loek Van Alphen, PH.D. in Support of Sanofi's Opposition to Motion to Amend" dated Nov. 14, 2018 from IPR Trial No. IPR2018-00187 for U. S. Pat. No. 9,492,559 (*Sanofi Pasteur Inc. and SK Chemicals Co., Ltd.* vs. *Pfizer, Inc.*), 78 pages.
Loek Van Alphen, "Exhibit 2073, Deposition of Loek Van Alphen, PH.D." dated Dec. 10, 2018 from IPR Trial No. PR2018-00187 for U. S. Pat. No. 9,492,559 (*Sanofi Pasteur Inc. and SK Chemicals Co., Ltd.* vs. *Pfizer, Inc.*), 201 pages.
Peter R. Paradiso, "Exhibit 1116, Deposition of Peter R. Paradiso, PH.D." dated Jan. 10, 2019 from IPR Trial No. PR2018-00187 for U. S. Pat. No. 9,492,559 (*Sanofi Pasteur Inc. and SK Chemicals Co., Ltd.* vs. *Pfizer, Inc.*), 125 pages.
Peter R. Paradiso, "Exhibit 2074, Declaration of Peter R. Paradiso, PH.D in Support of Pfizer's Reply in Support of Motion to Amend" dated Dec. 18, 2018 from IPR Trial No. IPR2018-00187 for U. S. Pat. No. 9,492,559 (*Sanofi Pasteur Inc. and SK Chemicals Co., Ltd.* vs. *Pfizer, Inc.*), 23 pages.
Chen et al., "Safety and immunogenicity of a new 13-valent pneumococcal conjugate vaccine versus a licensed 7-valent pneumococcal conjugate vaccine: a study protocol of a randomised non-inferiority trial in China", BMJ Open, Oct. 19, 2016, e012488, 9 pages.
International Search Report and Written Opinion dated Apr. 11, 2020 from International Application No. PCT/US2020/043729, (Authorized Officer, N. Renggli-Zulliger), 12 pages.
Beall et al., "A Population-Based Descriptive Atlas of Invasive Pneumococcal Strains Recovered Within the U.S. During 2015-2016", Frontiers in Microbiology, Nov. 19, 2018, vol. 9, 19 pages.
Van der Linden et al., "Increase of serotypes 15A and 23B in IPD in Germany in the PCV13 vaccination era", Bmc Infectious Diseases, May 5, 2015, vol. 15, No. 1, p. 207, 12 pages.
Non-Final Office Action dated May 3, 2023 for U.S. Appl. No. 17/471,825, 51 pages.
Dagan et al., "Reduction of Antibody Response to an 11-Valent Pneumococcal Vaccine Coadministered with a Vaccine Containing Acellular Pertussis Components", Infection and Immunity, Sep. 2004, vol. 72, No. 9, pp. 5383-5391.
N. Renggli-Zulliger (Authorized Officer), International Search Report and Written Opinion dated Nov. 4, 2020 for International Application No. PCT/US2020/043729, 12 pages.

\* cited by examiner

STREPTOCOCCUS PNEUMONIAE CAPSULAR POLYSACCHARIDES AND IMMUNOGENIC CONJUGATE THEREOF

CROSS-REFERENCE TO RELATED APPLICATIONS

The present application is a U.S. National Stage application of PCT/KR2019/004717 filed on Apr. 18, 2019, which claims the benefit of priority based on Korean Patent Application No. 10-2018-0045245 filed on Apr. 18, 2018, Korean Patent Application No. 10-2018-0045246 filed on Apr. 18, 2018, Korean Patent Application No. 10-2018-0045247 filed on Apr. 18, 2018, and Korean Patent Application No. 10-2018-0045248 filed on Apr. 18, 2018, and the entire contents disclosed in the description and drawings of the applications are incorporated herein by reference.

The present invention relates to an immunogenic composition and a vaccine of *Streptococcus pneumoniae*, and more specifically, the present invention relates to an immunogenic composition and a vaccine which comprise a capsular polysaccharide-carrier protein conjugate of *Streptococcus pneumoniae*.

BACKGROUND ART

*Streptococcus pneumoniae* is a major causative bacterium of pneumonia. In addition, it causes invasive diseases such as septicemia, bacteremia, meningitis and the like. According to National Statistical Office [2014 causes of death statistics], the death rate by pneumonia in 2014 was 23.7 people per hundred thousand people, and it increased 2.8 times compared with 2015, and the death rate by pneumonia has been continuously increasing. Furthermore, according to 2012 WHO, in 2008, 476,000 infants under the age of 5 who were HIV-negative died from *Streptococcus pneumoniae* infection globally, accounting for 5% of causes of death of infants under the age of 5. Pneumococcus is classified into more than about 90 serotypes, depending on structural and immunological characteristics of the capsular polysaccharide, which is a major virulence factor surrounding its outside (cell membrane).

To prevent diseases caused by *Streptococcus pneumoniae*, a 14-valent polysaccharide vaccine was developed by Dr. Robert Austrian in 1977, and after that, it was developed into a 23-valent polysaccharide vaccine. It has been demonstrated that a multivalent pneumococcus polysaccharide vaccine is useful for preventing *Streptococcus pneumoniae* diseases in the elderly and high-risk patients. However, infants and children do not have an immune response to most of *Streptococcus pneumoniae* polysaccharides, because of the T-cell independent immune response. Thus, a conjugate vaccine of a *Streptococcus pneumoniae* capsular polysaccharide and a carrier protein, which can cause a T-cell dependent response, has been developed.

The 7-valent *Streptococcus pneumoniae* conjugate vaccine (Prevnar®) comprises capsular polysaccharides derived from 7 most frequent serotypes 4, 6B, 9V, 14, 18C, 19F and 23F. It has been demonstrated that it is highly immunogenic and effective against invasive pneumococcal diseases and otitis media in infants and children, since it was primarily approved in America in 2000. After that, Prevnar 13®, the 13-valent conjugate vaccine in which 6 serotypes 1, 3, 5, 6A, 7F, 19A were added, and Synflorix, the 10-valent conjugate vaccine in which 3 serotypes 1, 5, 7F were added, have been developed in order, and the number of invasive diseases caused by *Streptococcus pneumoniae* was further reduced.

However, as the serotype change due to introduction of Prevnar, Prevnar 13 and Synflorix appeared and the number of diseases caused by serotypes comprised in a vaccine was generally reduced, the importance of non-vaccine serotypes which were of relatively low importance is rather emphasized.

In particular, the increase of incidence of invasive pneumococcal diseases caused by *Streptococcus pneumoniae* serotype 20 occurred in North America and Brazil (See, e.g., [Kendall B. et al., Vaccine. 34:474-478, 2016], [Yildirim I. et al., Pediatr Infect Dis J. 31(10): 1016-1021, 2012] or [Caieryo J. et al., PLoS ONE 9(10): e111129, 2014]). In addition, in the CASPER research conducted in Canada, the increase of incidence of serotypes 8 and 12F in addition to serotype 19A was observed (Sa-Leyo A. et al., J Clin Microbiol., 49(4): 1369-75, 2011). A recently announced research has reported that diseases caused by non-vaccine serotypes are increased after introduction of Prevnar 13 in Norway and Israel, and has exemplified 23A, 23B, 12F, 15A/15B/15C, 31, 33F, 7C, and 8 as such non-vaccine serotypes (Martin J., Pediatr Infect Dis J., 33(11):e286-90, 2014).

Despite the steady increase in incidence of pneumococcal diseases caused by *Streptococcus pneumoniae* serotypes 2, 9N, 17F, and/or 20, there is a lack of research that can effectively prevent or treat infection by serotypes.

Thus, there is an increasing need for an immunogenic conjugate and an immunogenic composition against non-vaccine serotypes comprising serotypes which are comprised in multivalent polysaccharide vaccines but are not comprised in conjugate vaccines to provide a broader protection range.

DISCLOSURE

Technical Problem

Accordingly, a problem to be solved by the present invention is to provide a multivalent vaccine capable of providing a wide range of protection.

In addition, it is also intended to provide an immunogenic composition comprising a new serotype that has not previously been comprised in a conjugate vaccine.

In addition, a problem to be solved by the present invention is to provide a pneumococcal conjugate vaccine having excellent antibody titer.

Technical Solution

One embodiment of the present invention provides an immunogenic composition comprising a *Streptococcus pneumoniae* polysaccharide-protein conjugate, comprising a capsular polysaccharide derived from one or more selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and a carrier protein conjugated to the each capsular polysaccharide.

One embodiment provides an immunogenic composition comprising a *Streptococcus pneumoniae* polysaccharide-protein conjugate, in which when the immunogenic composition comprises a polysaccharide derived from serotype 2, the polysaccharide is activated and binds to the carrier protein at a molecular weight of 100 to 400 kDa to form a conjugate, or when the immunogenic composition comprises a polysaccharide derived from serotype 17F, the polysaccharide is activated and binds to the carrier protein at a molecular weight of 400 to 900 kDa to form a conjugate, or when the immunogenic composition comprises a polysaccharide derived from serotype 20, the polysaccharide is activated and binds to the carrier protein at a molecular weight of 400 to 800 kDa to form a conjugate.

One embodiment of the present invention provides an immunogenic composition comprising a *Streptococcus pneumoniae* polysaccharide-protein conjugate, in which when the immunogenic composition comprises a polysaccharide derived from serotype 2, an immunogenic conjugate comprising a polysaccharide derived from serotype 2 has a molecular weight of 1,000 to 16,000 kDa, or when the immunogenic composition comprises a polysaccharide derived from serotype 17F, an immunogenic conjugate comprising a polysaccharide derived from serotype 17F has a molecular weight of 300 to 4,500 kDa, or when the immunogenic composition comprises a polysaccharide derived from serotype 20, an immunogenic conjugate comprising a polysaccharide derived from serotype 20 has a molecular weight of 1,000 to 4,000 kDa.

One embodiment of the present invention provides an immunogenic composition comprising a *Streptococcus pneumoniae* polysaccharide-protein conjugate, characterized by that the carrier protein is TT (Tetanus toxoid) or $CRM_{197}$, and preferably, an immunogenic composition comprising only one serotype may comprises $CRM_{197}$ as the carrier protein.

One embodiment of the present invention provides an immunogenic composition comprising a *Streptococcus pneumoniae* polysaccharide-protein conjugate, in which when the immunogenic composition comprises a polysaccharide derived from serotype 2, the ratio of the serotype 2 capsular polysaccharide to the carrier protein in the immunogenic conjugate (polysaccharide/protein, W/W) is 0.5 to 2.0, or when the immunogenic composition comprises a polysaccharide derived from serotype 17F, the ratio of the serotype 17F capsular polysaccharide to the carrier protein in the immunogenic conjugate (polysaccharide/protein, W/W) is 0.5 to 18, or when the immunogenic composition comprises a polysaccharide derived from serotype 20, the ratio of the serotype 20 capsular polysaccharide to the carrier protein in the immunogenic conjugate (polysaccharide/protein, W/W) is 1 to 5.

One embodiment of the present invention provides an immunogenic composition comprising a *Streptococcus pneumoniae* polysaccharide-protein conjugate, in which 20 to 60% of the total molecular weight is present within 0.3 Kd in a CL-4B column, in case of the immunogenic conjugate comprising a polysaccharide derived from serotype 2, or 15 to 60% of the total molecular weight is present within 0.3 Kd in a CL-4B column, in case of the immunogenic conjugate comprising a polysaccharide derived from serotype 17F, or 70 to 90% of the total molecular weight is present within 0.3 Kd in a CL-4B column, in case of the immunogenic conjugate comprising a polysaccharide derived from serotype 20.

One embodiment of the present invention provides an immunogenic composition comprising a *Streptococcus pneumoniae* polysaccharide-protein conjugate, in which the degree of oxidation of the polysaccharide conjugated to the conjugate is 2 to 18, in case of the immunogenic conjugate comprising a polysaccharide derived from serotype 2, or the degree of oxidation of the polysaccharide conjugated to the conjugate is 1 to 22, in case of the immunogenic conjugate comprising a polysaccharide derived from serotype 17F, or the degree of oxidation of the polysaccharide conjugated to the conjugate is 4 to 16, in case of the immunogenic conjugate comprising a polysaccharide derived from serotype 20.

One embodiment of the present invention provides an immunogenic composition comprising a *Streptococcus pneumoniae* polysaccharide-protein conjugate, in which the immunogenic composition is that polysaccharides derived from 15 serotypes different each other are conjugated to respective carrier proteins, and the serotypes are 1, 2, 3, 4, 5, 6A, 6B, 7F, 9N, 9V, 14, 18C, 19A, 19F, and 23F, and the serotypes are conjugated to CRM 197.

One embodiment of the present invention provides an immunogenic composition comprising a *Streptococcus pneumoniae* polysaccharide-protein conjugate, in which the immunogenic composition is that polysaccharides derived from 23 serotypes different each other are conjugated to respective carrier proteins, and the serotypes are 1, 2, 6A, 6B, 7F, 8, 9N, 9V, 10A, 11A, 12F, 14, 15B, 17F, 18C, 19A, 19F, 20, 22F, 23F, and 33F, and among the serotypes, capsular polysaccharides derived from serotypes 3 and 5 are conjugated to carrier protein TT and capsular polysaccharides derived from serotypes 1, 2, 6A, 6B, 7F, 8, 9N, 9V, 10A, 11A, 12F, 14, 15B, 17F, 18C, 19A, 19F, 20, 22F, 23F, and 33F are conjugated to carrier protein CRM197.

One embodiment of the present invention provides an immunogenic composition comprising a *Streptococcus pneumoniae* polysaccharide-protein conjugate, in which the immunogenic composition is that polysaccharides derived from 24 serotypes different each other are conjugated to respective carrier proteins, and the serotypes are 2, 3, 4, 6A, 6B, 7F, 8, 9N, 9V, 10A, 11A, 12F, 14, 15B, 17F, 18C, 19A, 19F, 20, 22F, 23F, and 33F, and capsular polysaccharides derived from serotypes 1 and 5 are conjugated to carrier protein TT and capsular polysaccharides derived from serotypes 2, 3, 4, 6A, 6B, 7F, 8, 9N, 9V, 10A, 11A, 12F, 14, 15B, 17F, 18C, 19A, 19F, 20, 22F, 23F, and 33F are conjugated to carrier protein CRM197.

One embodiment of the present invention provides an immunogenic composition comprising a *Streptococcus pneumoniae* polysaccharide-protein conjugate, which comprises a physiologically acceptable vehicle.

One embodiment of the present invention provides an immunogenic composition comprising a *Streptococcus pneumoniae* polysaccharide-protein conjugate, in which the immunogenic composition is a vaccine.

One embodiment of the present invention provides a preparation method of an immunogenic composition comprising a *Streptococcus pneumoniae* polysaccharide-protein conjugate comprising (a) a step of fermenting and dissolving a bacterial cell which produces a capsular polysaccharide derived from one or more serotypes selected from the group consisting of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F;

(b) a step of purifying a capsular polysaccharide derived from *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F in the dissolved cell;

(c) a step of reacting the purified polysaccharide with an oxidizing agent to activate it; and (d) a step of combining the activated polysaccharide with a carrier protein to form a *Streptococcus pneumoniae* polysaccharide-protein conjugate bound to the carrier protein.

In one embodiment of the present invention, the preparation method may further comprise a step of hydrolyzing the purified *Streptococcus pneumoniae* capsular polysaccharide to size it, before the (c) step, in case of the capsular polysaccharides derived from serotypes 2 and 17F.

One embodiment of the present invention provides a preparation method of an immunogenic composition comprising a *Streptococcus pneumoniae* polysaccharide-protein conjugate, characterized by that the combined carrier protein of the (d) step forms a conjugate with the polysaccharide activated by reacting with one or more reducing agents selected from the group consisting of cyanoborohydride, borane-pyridine and borohydride exchange resin.

One embodiment of the present invention provides a preparation method of an immunogenic composition comprising a *Streptococcus pneumoniae* polysaccharide-protein conjugate, characterized by that the (c) step is reacting 0.01~0.22 μg of periodate per 1 μg polysaccharide at a temperature of 20 to 25° C. for 15 to 20 hours.

One embodiment of the present invention provides a *Streptococcus pneumoniae* polysaccharide-protein conjugate for preventing or treating *Streptococcus pneumoniae* infection, obtained by the method.

One embodiment of the present invention provides a method for preventing or treating infection of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F in a subject, by administering an effective dose of an immunogenic composition comprising a *Streptococcus pneumoniae* polysaccharide-protein conjugate, comprising a capsular polysaccharide derived from one or more selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and one or 2 or more of carrier proteins conjugated to the respective capsular polysaccharide, into a subject. The and/or means 'and' or 'or'.

The method may prevent or treat infection against one or more serotypes selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, or it may be one or more, and it may prevent infection against 15 serotypes, or it may prevent infection against 23 serotypes, or it may prevent infection against 24 serotypes.

One example of the present invention provides a use for prevention or treatment of pneumococcal infection of a *Streptococcus pneumoniae* polysaccharide-protein conjugate, comprising a capsular polysaccharide derived from one or more selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and one or 2 or more of carrier proteins conjugated to the respective capsular polysaccharide.

One example of the present invention provides an immunogenic conjugate of *Streptococcus pneumoniae* serotype 2, comprising a capsular polysaccharide of serotype 2, derived from *Streptococcus pneumoniae*; and a carrier protein bound to the capsular polysaccharide.

The polysaccharide of serotype 2 may be activated and bind to the carrier protein at a molecular weight of 100 to 400 kDa to form a conjugate.

In one example of the present invention, the immunogenic conjugate may have a molecular weight of 1,000 to 16,000 kDa, and for example, the carrier protein may be $CRM_{197}$.

In one example of the present invention, the ratio of serotype 2 capsular polysaccharide to the carrier protein in the immunogenic conjugate (W/W) may be 0.5 to 2.0.

20 to 60% of the immunogenic conjugate of serotype 2 may be present within 0.3 Kd in a CL-4 B column. Another example provides an immunogenic conjugate of *Streptococcus pneumoniae* serotype 2 having a degree of oxidation of 2 to 18.

When the polysaccharide of *Streptococcus pneumoniae* serotype 2 is oxidized by adding 0.02 to 0.12 μg of periodate per 1 μg of the sugar content and is conjugated to a protein, the molecular weight of the conjugate may be 1,000~16,000 kDa, and the distribution of the molecular weight may be 20~60% (0.3 kd or less), and the ratio of polysaccharide/protein may be 0.5 to 2.0.

One example of the present invention may provide an immunogenic composition comprising the immunogenic conjugate and a physiologically acceptable vehicle.

Other example of the present invention may provide a vaccine comprising the immunogenic composition.

Other example of the present invention may provide a preparation method of an immunogenic conjugate of *Streptococcus pneumoniae* serotype 2, comprising (a) a step of fermenting and dissolving a bacterial cell producing a *Streptococcus pneumoniae* serotype 2 capsular polysaccharide;

(b) a step of purifying the *Streptococcus pneumoniae* serotype 2 capsular polysaccharide in the dissolved cell;

(c) a step of hydrolyzing the purified *Streptococcus pneumoniae* serotype 2 capsular polysaccharide to size the polysaccharide;

(d) a step of reacting the sized polysaccharide of the (c) step to activate the polysaccharide; and (e) a step of combining the activated polysaccharide with a carrier protein to form a conjugate of *Streptococcus pneumoniae* serotype 2 capsular polysaccharide bound to the carrier protein.

The carrier protein combined of the (e) step may form a conjugate with the activated polysaccharide by reacting it with a reducing agent.

The (d) step may comprise a process of reacting 0.02~0.12 μg of periodate per 1 μg polysaccharide at a temperature of 20 to 25° C. for 15 to 20 hours.

The activated polysaccharide to be combined with the carrier protein of the (e) step may have a molecular weight of 100 to 400 kDa.

A preparation method of an immunogenic conjugate of *Streptococcus pneumoniae* serotype 2, in which the carrier protein is CRM197, may be provided.

The immunogenic conjugate may have a molecular weight of 1,000 to 16,000 kDa.

In one example, the initial input ratio of the activated serotype 2 capsular polysaccharide versus the carrier protein (carrier protein:polysaccharide) may be 0.5 to 2:1.

Other example may provide a preparation method of an immunogenic conjugate of *Streptococcus pneumoniae* serotype 2, in which at least 20 to 60% of the immunogenic conjugate is present within 0.3 Kd in a CL-4B column.

One example of the present invention may provide an immunogenic conjugate obtained by the method.

One example of the present invention may provide an immunogenic composition comprising an immunogenic conjugate obtained by the method and a physiologically acceptable vehicle.

Other example may provide a vaccine comprising the immunogenic composition.

The present invention provides an immunogenic conjugate of *Streptococcus pneumoniae* serotype 9N, comprising a capsular polysaccharide of serotype 9N, derived from *Streptococcus pneumoniae*; and a carrier protein bound to the capsular polysaccharide.

In one example of the present invention, the polysaccharide of serotype 9N may be activated and bind to the carrier protein at a molecular weight of 200 to 700 kDa to form a conjugate.

The immunogenic conjugate may have a molecular weight of 500 to 4,000 kDa and the carrier protein may be $CRM_{197}$.

The ratio of the serotype 9N capsular polysaccharide to the carrier protein in the immunogenic conjugate (W/W) is 0.1 to 5, and preferably, it may be 0.5~2.5.

In one example, 15 to 60% of the immunogenic conjugate may be present within 0.3 Kd in a CL-4 B column.

In one example, the conjugate may have a degree of oxidation of 2 to 19. In one example of the present invention, when the polysaccharide of *Streptococcus pneumoniae* serotype 9N is oxidized by adding 0.02~0.19 μg of periodate per 1 μg of the sugar content and is conjugated with a protein, the molecular weight of the conjugate may be 500~4,000 kDa, and the distribution of the molecular weight may be 15~60% (0.3 kd or less), and the polysaccharide/protein ratio may be 0.5~2.5.

One example of the present invention may provide an immunogenic composition comprising an immunogenic conjugate and a physiologically acceptable vehicle.

Other example of the present invention may provide a vaccine comprising the immunogenic composition.

Other example of the present invention may provide a preparation method of an immunogenic conjugate of *Streptococcus pneumoniae* serotype 9N, comprising
(a) a step of fermenting and dissolving a bacterial cell producing a *Streptococcus pneumoniae* serotype 9N capsular polysaccharide;
(b) a step of purifying the *Streptococcus pneumoniae* serotype 9N capsular polysaccharide in the dissolved cell;
(c) a step of reacting the polysaccharide with an oxidizing agent to activate it; and
(d) a step of combining the activated polysaccharide with a carrier protein to form a conjugate of *Streptococcus pneumoniae* serotype 9N capsular polysaccharide bound to the carrier protein.

A preparation method of an immunogenic conjugate of *Streptococcus pneumoniae* serotype 9N, characterized by that the combined carrier protein of the (d) step is reacted with a reducing agent to form a conjugate with the activated polysaccharide, may be provided.

The (c) step may comprise a process of reacting 0.02~0.19 μg of periodate per 1 μg of polysaccharide at a temperature of 20 to 25° C. for 15 to 20 hours.

The polysaccharide reacting with the oxidizing agent of the (c) step may have a molecular weight of 400 to 900 kDa.

The activated polysaccharide to be combined with the carrier protein of the (d) step may have a molecular weight of 200-700 kDa.

The immunogenic conjugate may have a molecular weight of 500 to 4,000 kDa.

The initial input ratio of the activated serotype 9N capsular polysaccharide versus the carrier protein (carrier protein:polysaccharide) may be 0.5 to 2.5:1.

In one example, at least 15 to 60% of the immunogenic conjugate may be present within 0.3 Kd in a CL-4B column.

One example of the present invention may provide an immunogenic conjugate obtained by the method. One example of the present invention may provide an immunogenic composition comprising an immunogenic conjugate obtained by the method and a physiologically acceptable vehicle. Other example may provide a vaccine comprising the immunogenic composition.

One example of the present invention provides an immunogenic conjugate of *Streptococcus pneumoniae* serotype 17F, comprising a capsular polysaccharide of serotype 17F, derived from *Streptococcus pneumoniae*; and a carrier protein bound to the capsular polysaccharide.

The polysaccharide of serotype 17F may be activated and bind to the carrier protein at a molecular weight of 400 to 900 kDa to form a conjugate.

In one example of the present invention, the immunogenic conjugate may have a molecular weight of 300 to 4,500 kDa, and for example, the carrier protein may be $CRM_{197}$.

In one example of the present invention, the ratio of the serotype 17F capsular polysaccharide to the carrier protein in the immunogenic conjugate (W/W) may be 0.5 to 18.

15 to 60% of the immunogenic conjugate of serotype 17F may be present within 0.3 Kd in a CL-4 B column. Another example provides an immunogenic conjugate of *Streptococcus pneumoniae* serotype 17F having a degree of oxidation of 1 to 22.

When the polysaccharide of *Streptococcus pneumoniae* serotype 17F is oxidized by adding 0.01 to 0.22 μg of periodate per 1 μg of the sugar content and is conjugated with a protein, the molecular weight of the conjugate may be 300 to 4,500 kDa, and the distribution of the molecular weight may be 15~60% (0.3 kd or less), and the polysaccharide/protein ratio may be 0.5 to 18.

One example of the present invention may provide an immunogenic composition comprising the immunogenic conjugate and a physiological acceptable vehicle.

Other example of the present invention may provide a vaccine comprising the immunogenic composition.

Other example of the present invention may provide a preparation method of an immunogenic conjugate of *Streptococcus pneumoniae* serotype 17F, comprising
(a) a step of fermenting and dissolving a bacterial cell producing a *Streptococcus pneumoniae* serotype 17F capsular polysaccharide;
(b) a step of purifying the *Streptococcus pneumoniae* serotype 17F capsular polysaccharide in the dissolved cell;
(c) a step of hydrolyzing the purified *Streptococcus pneumoniae* serotype 17F capsular polysaccharide to size the polysaccharide;
(d) a step of reacting the sized polysaccharide of the (c) step to activate the polysaccharide; and
(e) a step of combining the activated polysaccharide with a carrier protein to form a conjugate of *Streptococcus pneumoniae* serotype 17F capsular polysaccharide bound to the carrier protein.

A preparation method of an immunogenic conjugate of *Streptococcus pneumoniae* serotype 17F, characterized by that the carrier protein combined of the (e) step may form a conjugate with the activated polysaccharide by reacting it with a reducing agent, may be provided.

The (d) step may comprise a process of reacting 0.01~0.22 μg of periodate per 1 μg polysaccharide at a temperature of 20 to 25° C. for 15 to 20 hours.

The activated polysaccharide to be combined with the carrier protein of the (e) step may have a molecular weight of 400 to 900 kDa.

The immunogenic conjugate may have a molecular weight of 300 to 4,500 kDa.

The initial input ratio of the activated serotype 17F capsular polysaccharide versus the carrier protein (carrier protein:polysaccharide) may be 1:1.

In one example, at least 15 to 60% of the immunogenic conjugate molecular weight may be present within 0.3 Kd in a CL-4B column.

One example of the present invention may provide an immunogenic conjugate obtained by the method. One example of the present invention may provide an immunogenic composition comprising an immunogenic conjugate obtained by the method and a physiologically acceptable vehicle. Other example may provide a vaccine comprising the immunogenic composition.

One example of the present invention provides an immunogenic conjugate of *Streptococcus pneumoniae* serotype 20, comprising a capsular polysaccharide of serotype 20, derived from of *Streptococcus pneumoniae*; and a carrier protein bound to the capsular polysaccharide.

The polysaccharide of serotype 20 may be activated and bind to the carrier protein at a molecular weight of 400 to 800 kDa to form a conjugate.

In one example of the present invention, the immunogenic conjugate may have a molecular weight of 1,000 to 4,000 kDa, and for example, the carrier protein may be $CRM_{197}$.

In one example of the present invention, the ratio of the serotype 20 capsular polysaccharide to the carrier protein in the immunogenic conjugate (W/W) may be 1 to 5.

70 to 90% of the immunogenic conjugate of serotype 20 may be present within 0.3 Kd in a CL-4 B column. Another example provides an immunogenic conjugate of *Streptococcus pneumoniae* serotype 20 having a degree of oxidation of 4 to 16.

When the polysaccharide of *Streptococcus pneumoniae* serotype 20 is oxidized by adding 0.01 to 0.04 μg of periodate per 1 μg of the sugar content and is conjugated with a protein, the molecular weight of the conjugate may be 1,000 to 4,000 kDa, and the distribution of the molecular weight may be 70~90% (0.3 kd or less), and the polysaccharide/protein ratio may be 1 to 5.

One example of the present invention may provide an immunogenic composition comprising the immunogenic conjugate and a physiological acceptable vehicle.

Other example of the present invention may provide a vaccine comprising the immunogenic composition.

Other example of the present invention may provide a preparation method of an immunogenic conjugate of *Streptococcus pneumoniae* serotype 20, comprising (a) a step of fermenting and dissolving a bacterial cell producing a *Streptococcus pneumoniae* serotype 20 capsular polysaccharide;

(b) a step of purifying the *Streptococcus pneumoniae* serotype 20 capsular polysaccharide in the dissolved cell;

(c) a step of reacting the polysaccharide with an oxidizing agent to activate it; and (d) a step of combining the activated polysaccharide with a carrier protein to form a conjugate of *Streptococcus pneumoniae* serotype 20 capsular polysaccharide bound to the carrier protein.

The carrier protein combined of the (d) step may be reacted with a reducing agent to form a conjugate with the activated polysaccharide.

The (c) step may comprise a process of reacting 0.01~0.04 μg of periodate per 1 μg polysaccharide at a temperature of 20 to 25° C. for 15 to 20 hours.

The activated polysaccharide to be combined with the carrier protein of the (d) step may have a molecular weight of 400 to 800 kDa.

In one example of the present invention, the immunogenic conjugate of the present invention by the method may have a molecular weight of 1,000 to 4,000 kDa.

The initial input ratio of the activated serotype 20 capsular polysaccharide versus the carrier protein (carrier protein: polysaccharide) may be 1:1.

In one example, at least 70 to 90% of the immunogenic conjugate molecular weight may be present within 0.3 Kd in a CL-4B column.

One example of the present invention may provide an immunogenic conjugate obtained by the method.

One example may provide an immunogenic composition comprising an immunogenic conjugate obtained by the method and a physiologically acceptable vehicle.

Other example may provide a vaccine comprising the immunogenic composition.

One embodiment of the present invention provides an immunogenic composition comprising a *Streptococcus pneumoniae* polysaccharide-protein conjugate, comprising a capsular polysaccharide derived from one or more selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and a carrier protein conjugated to the respective capsular polysaccharide.

One embodiment provides an immunogenic composition comprising a *Streptococcus pneumoniae* polysaccharide-protein conjugate, in which when the immunogenic composition comprises a polysaccharide derived from serotype 2, the polysaccharide is activated and binds to the carrier protein at a molecular weight of 100 to 400 kDa to form a conjugate, or when the immunogenic composition comprises a polysaccharide derived from serotype 17F, the polysaccharide is activated and binds to the carrier protein at a molecular weight of 400 to 900 kDa to form a conjugate, or when the immunogenic composition comprises a polysaccharide derived from serotype 20, the polysaccharide is activated and binds to the carrier protein at a molecular weight of 400 to 800 kDa to form a conjugate.

One embodiment of the present invention provides an immunogenic composition comprising a *Streptococcus pneumoniae* polysaccharide-protein conjugate, in which when the immunogenic composition comprises a polysaccharide derived from serotype 2, an immunogenic conjugate comprising a polysaccharide derived from serotype 2 has a molecular weight of 1,000 to 16,000 kDa, or when the immunogenic composition comprises a polysaccharide derived from serotype 17F, an immunogenic conjugate comprising a polysaccharide derived from serotype 17F has a molecular weight of 300 to 4,500 kDa, or when the immunogenic composition comprises a polysaccharide derived from serotype 20, an immunogenic conjugate comprising a polysaccharide derived from serotype 20 has a molecular weight of 1,000 to 4,000 kDa.

One embodiment of the present invention provides an immunogenic composition comprising a *Streptococcus pneumoniae* polysaccharide-protein conjugate, characterized by that the carrier protein is TT (Tetanus toxoid) or CRM$_{197}$, and preferably, an immunogenic composition comprising only one serotype may comprises CRM$_{197}$ as the carrier protein.

One embodiment of the present invention provides an immunogenic composition comprising a *Streptococcus pneumoniae* polysaccharide-protein conjugate, in which when the immunogenic composition comprises a polysaccharide derived from serotype 2, the ratio of the serotype 2 capsular polysaccharide to the carrier protein in the immunogenic conjugate (polysaccharide/protein, W/W) is 0.5 to 2.0, or when the immunogenic composition comprises a polysaccharide derived from serotype 17F, the ratio of the serotype 17F capsular polysaccharide to the carrier protein in the immunogenic conjugate (polysaccharide/protein, W/W) is 0.5 to 18, or when the immunogenic composition comprises a polysaccharide derived from serotype 20, the ratio of the serotype 20 capsular polysaccharide to the carrier protein in the immunogenic conjugate (polysaccharide/protein, W/W) is 1 to 5.

One embodiment of the present invention provides an immunogenic composition comprising a *Streptococcus pneumoniae* polysaccharide-protein conjugate, in which 20 to 60% of the total molecular weight is present within 0.3 Kd in a CL-4B column, in case of the immunogenic conjugate comprising a polysaccharide derived from serotype 2, or 15 to 60% of the total molecular weight is present within 0.3 Kd in a CL-4B column, in case of the immunogenic conjugate comprising a polysaccharide derived from serotype 17F, or 70 to 90% of the total molecular weight is present within 0.3 Kd in a CL-4B column, in case of the immunogenic conjugate comprising a polysaccharide derived from serotype 20.

One embodiment of the present invention provides an immunogenic composition comprising a *Streptococcus pneumoniae* polysaccharide-protein conjugate, in which the degree of oxidation of the polysaccharide conjugated to the conjugate is 2 to 18, in case of the immunogenic conjugate comprising a polysaccharide derived from serotype 2, or the degree of oxidation of the polysaccharide conjugated to the conjugate is 1 to 22, in case of the immunogenic conjugate comprising a polysaccharide derived from serotype 17F, or the degree of oxidation of the polysaccharide conjugated to the conjugate is 4 to 16, in case of the immunogenic conjugate comprising a polysaccharide derived from serotype 20.

One embodiment of the present invention provides an immunogenic composition comprising a *Streptococcus pneumoniae* polysaccharide-protein conjugate, in which the immunogenic composition is that polysaccharides derived from 15 serotypes different each other are conjugated to the respective carrier proteins, and the serotypes are 1, 2, 3, 4, 5, 6A, 6B, 7F, 9N, 9V, 14, 18C, 19A, 19F, and 23F, and the serotypes are conjugated with CRM 197.

One embodiment of the present invention provides an immunogenic composition comprising a *Streptococcus pneumoniae* polysaccharide-protein conjugate, in which the immunogenic composition is that polysaccharides derived from 23 serotypes different each other are conjugated to the respective carrier proteins, and the serotypes are 1, 2, 6A, 6B, 7F, 8, 9N, 9V, 10A, 11A, 12F, 14, 15B, 17F, 18C, 19A, 19F, 20, 22F, 23F, and 33F, and among the serotypes, the capsular polysaccharides derived from serotypes 3 and 5 are conjugated to the carrier protein TT, and the capsular polysaccharides derived from serotypes 1, 2, 6A, 6B, 7F, 8, 9N, 9V, 10A, 11A, 12F, 14, 15B, 17F, 18C, 19A, 19F, 20, 22F, 23F, and 33F are conjugated to the carrier protein CRM197.

One embodiment of the present invention provides an immunogenic composition comprising a *Streptococcus pneumoniae* polysaccharide-protein conjugate, in which the immunogenic composition is that polysaccharides derived from 24 serotypes different each other are conjugated to the respective carrier proteins, and the serotypes are 2, 3, 4, 6A, 6B, 7F, 8, 9N, 9V, 10A, 11A, 12F, 14, 15B, 17F, 18C, 19A, 19F, 20, 22F, 23F, and 33F, and among the serotypes, the capsular polysaccharides derived from serotypes 1 and 5 are conjugated to the carrier protein TT, and the capsular polysaccharides derived from serotypes 2, 3, 4, 6A, 6B, 7F, 8, 9N, 9V, 10A, 11A, 12F, 14, 15B, 17F, 18C, 19A, 19F, 20, 22F, 23F, and 33F are conjugated to the carrier protein CRM197.

One embodiment of the present invention provides an immunogenic composition comprising a *Streptococcus pneumoniae* polysaccharide-protein conjugate, in which the immunogenic composition comprises a physiologically acceptable vehicle.

One embodiment of the present invention provides an immunogenic composition comprising a *Streptococcus pneumoniae* polysaccharide-protein conjugate, characterized by that the immunogenic composition is a vaccine.

One embodiment of the present invention provides a preparation method of an immunogenic composition comprising a *Streptococcus pneumoniae* polysaccharide-protein conjugate, comprising (a) a step of fermenting and dissolving a bacterial cell producing a capsular polysaccharide derived from one or more serotypes selected from the group consisting of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F;

(b) a step of purifying a capsular polysaccharide derived from *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F in the dissolved cell;

(c) a step of reacting the purified polysaccharide with an oxidizing agent to activate it; and (d) a step of combining the activated polysaccharide with a carrier protein to form a *Streptococcus pneumoniae* polysaccharide-protein conjugate bound to the carrier protein.

In one embodiment of the present invention, the preparation method may further comprise a step of hydrolyzing the purified capsular polysaccharide of *Streptococcus pneumoniae* to size the polysaccharide, before the (c) step, in case of capsular polysaccharides derived from serotypes 2 and 17F.

One embodiment of the present invention provides a preparation method of an immunogenic composition comprising a *Streptococcus pneumoniae* polysaccharide-protein conjugate, characterized by that the combined carrier protein of the (d) step forms a conjugate with the polysaccharide activated by reacting it with one or more reducing agents selected from the group consisting of cyanoborohydride, borane-pyridine, and borohydride exchange resin.

One embodiment of the present invention provides a preparation method of an immunogenic composition comprising a *Streptococcus pneumoniae* polysaccharide-protein conjugate, characterized by that the (c) step is reacting 0.01~0.22 μg of periodate per 1 μg of polysaccharide at a temperature of 20 to 25° C. for 15 to 20 hours.

One embodiment of the present invention provides a *Streptococcus pneumoniae* polysaccharide-protein conjugate for preventing or treating *Streptococcus pneumoniae* infection obtained by the method.

One embodiment may provide a method for preventing or treating infection of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F in a subject, by administering an effective dose of an immunogenic composition comprising a *Streptococcus pneumoniae* polysaccharide-protein conjugate, comprising a capsular polysaccharide derived from one or more selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and one or 2 or more of carrier proteins conjugated to the respective capsular polysaccharide. The and/or means 'and' or 'or'.

The method may prevent or treat infection against one or more serotypes selected from the group consisting of serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, or it may be one or more, and it may prevent infection against 15 serotypes, or it may prevent infection against 23 serotypes, or it may prevent infection against 24 serotypes.

One example of the present invention provides a use for prevention or treatment of pneumococcal infection of a *Streptococcus pneumoniae* polysaccharide-protein conjugate, comprising a capsular polysaccharide derived from one or more selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F, derived from *Streptococcus pneumoniae*; and one or 2 or more of carrier proteins conjugated to the respective capsular polysaccharide.

One example of the present invention provides an immunogenic conjugate of *Streptococcus pneumoniae* serotype 2, comprising a capsular polysaccharide of serotype 2, derived from *Streptococcus pneumoniae*; and a carrier protein bound to the capsular polysaccharide.

The polysaccharide of serotype 2 may be activated and bind to the carrier protein at a molecular weight of 100 to 400 kDa to form a conjugate.

In one example of the present invention, the immunogenic conjugate may have a molecular weight of 1,000 to 16,000 kDa, and for example, the carrier protein may be $CRM_{197}$.

In one example of the present invention, the ratio of the serotype 2 capsular polysaccharide to the carrier protein in the immunogenic conjugate (W/W) may be 0.5 to 2.0.

20 to 60% of the immunogenic conjugate of serotype 2 may be present within 0.3 Kd in a CL-4B column. Another example provides an immunogenic conjugate of *Streptococcus pneumoniae* serotype 2 having a degree of oxidation of 2 to 18.

When the polysaccharide of *Streptococcus pneumoniae* serotype 2 is oxidized by adding 0.02 to 0.12 μg of periodate per 1 μg of the sugar content and is conjugate with a protein, the molecular weight of the conjugate may be 1,000~16,000 kDa, and the distribution of the molecular weight may be 20~60% (0.3 kd or less), and the polysaccharide/protein ratio may be 0.5 to 2.0.

One example of the present invention may provide an immunogenic composition comprising the immunogenic conjugate and a physiologically acceptable vehicle.

Other example of the present invention may provide a vaccine comprising the immunogenic composition.

Other example of the present invention may provide a vaccine comprising the immunogenic composition.

Other example of the present invention may provide a preparation method of an immunogenic conjugate of *Streptococcus pneumoniae* serotype 2, comprising (a) a step of fermenting and dissolving a bacterial cell producing a *Streptococcus pneumoniae* serotype 2 capsular polysaccharide;

(b) a step of purifying the *Streptococcus pneumoniae* serotype 2 capsular polysaccharide in the dissolved cell;

(c) a step of hydrolyzing the purified *Streptococcus pneumoniae* serotype 2 capsular polysaccharide to size the polysaccharide;

(d) a step of reacting the sized polysaccharide of the (c) step to activate the polysaccharide; and (e) a step of combining the activated polysaccharide with a carrier protein to form a conjugate of *Streptococcus pneumoniae* serotype 2 capsular polysaccharide bound to the carrier protein.

The carrier protein combined of the (e) step may form a conjugate with the activated polysaccharide by reacting it with a reducing agent.

The (d) step may comprise a process of reacting 0.02~0.12 μg of periodate per 1 μg polysaccharide at a temperature of 20 to 25° C. for 15 to 20 hours.

The activated polysaccharide combined to the carrier protein of the (e) step may have a molecular weight of 100 to 400 kDa.

A preparation method of an immunogenic conjugate of *Streptococcus pneumoniae* serotype 2, in which the carrier protein is CRM197, may be provided.

The immunogenic conjugate may have a molecular weight of 1,000 to 16,000 kDa.

In one example, the initial input ratio of the activated serotype 2 capsular polysaccharide versus the carrier protein (carrier protein:polysaccharide) may be 0.5 to 2:1.

Other example may provide a preparation method of an immunogenic conjugate of *Streptococcus pneumoniae* serotype 2, in which at least 20 to 60% of the immunogenic conjugate is present within 0.3 Kd in a CL-4B column.

One example of the present invention may provide an immunogenic conjugate obtained by the method.

One example of the present invention may provide an immunogenic composition comprising an immunogenic conjugate obtained by the method and a physiologically acceptable vehicle.

Other example may provide a vaccine comprising the immunogenic composition.

The present invention provides an immunogenic conjugate of *Streptococcus pneumoniae* serotype 9N, comprising a capsular polysaccharide of serotype 9N, derived from *Streptococcus pneumoniae*; and a carrier protein bound to the capsular polysaccharide.

In one example of the present invention, the polysaccharide of serotype 9N may be activated and bind to the carrier protein at a molecular weight of 200 to 700 kDa to form a conjugate.

The immunogenic conjugate may have a molecular weight of 500 to 4,000 kDa and the carrier protein may be $CRM_{197}$.

The ratio of the serotype 9N capsular polysaccharide to the carrier protein in the immunogenic conjugate (W/W) may be 0.1 to 5, and preferably, it may be 0.5~2.5.

In one example, 15 to 60% of the immunogenic conjugate may be present within 0.3 Kd in a CL-4B column.

In one example, the conjugate may have a degree of oxidation of 2 to 19.

In one example of the present invention, when the polysaccharide of Streptococcus pneumoniae serotype 9N is oxidized by adding 0.02~0.19 μg of periodate per 1 μg of the sugar content and is conjugated with a protein, the molecular weight of the conjugate may be 500~4,000 kDa, and the distribution of the molecular weight may be 15~60% (0.3 kd or less), and the polysaccharide/protein ratio may be 0.5~2.5.

One example of the present invention may provide an immunogenic composition comprising an immunogenic conjugate and a physiologically acceptable vehicle.

Other example of the present invention may provide a vaccine comprising the immunogenic composition.

Other example of the present invention may provide a preparation method of an immunogenic conjugate of Streptococcus pneumoniae serotype 9N, comprising (a) a step of fermenting and dissolving a bacterial cell producing a Streptococcus pneumoniae serotype 9N capsular polysaccharide;

(b) a step of purifying the Streptococcus pneumoniae serotype 9N capsular polysaccharide in the dissolved cell;

(c) a step of reacting the polysaccharide with an oxidizing agent to activate it; and (d) a step of combining the activated polysaccharide with a carrier protein to form a conjugate of Streptococcus pneumoniae serotype 9N capsular polysaccharide bound to the carrier protein.

A preparation method of an immunogenic conjugate of Streptococcus pneumoniae serotype 9N, characterized by that the combined carrier protein of the (d) step is reacted with a reducing agent to form a conjugate with the activated polysaccharide, may be provided.

The (c) step may comprise a process of reacting 0.02~0.19 μg of periodate per 1 μg of polysaccharide at a temperature of 20 to 25° C. for 15 to 20 hours.

The polysaccharide reacting with the oxidizing agent of the (c) step may have a molecular weight of 400 to 900 kDa.

The activated polysaccharide to be combined with the carrier protein of the (d) step may have a molecular weight of 200-700 kDa.

The immunogenic conjugate may have a molecular weight of 500 to 4,000 kDa.

The initial input ratio of the activated serotype 9N capsular polysaccharide versus the carrier protein (carrier protein:polysaccharide) may be 0.5 to 2.5:1.

In one example, at least 15 to 60% of the immunogenic conjugate may be present within 0.3 Kd in a CL-4B column.

One example of the present invention may provide an immunogenic conjugate obtained by the method. One example of the present invention may provide an immunogenic composition comprising an immunogenic conjugate obtained by the method and a physiologically acceptable vehicle. Other example may provide a vaccine comprising the immunogenic composition.

One example of the present invention provides an immunogenic conjugate of Streptococcus pneumoniae serotype 17F, comprising a capsular polysaccharide of serotype 17F, derived from Streptococcus pneumoniae; and a carrier protein bound to the capsular polysaccharide.

The polysaccharide of serotype 17F may be activated and bind to the carrier protein at a molecular weight of 400 to 900 kDa to form a conjugate.

In one example of the present invention, the immunogenic conjugate may have a molecular weight of 300 to 4,500 kDa, and for example, the carrier protein may be $CRM_{197}$.

In one example of the present invention, the ratio of the serotype 17F capsular polysaccharide to the carrier protein in the immunogenic conjugate (W/W) may be 0.5 to 18.

15 to 60% of the immunogenic conjugate of serotype 17F may be present within 0.3 Kd in a CL-4B column. Another example provides an immunogenic conjugate of Streptococcus pneumoniae serotype 17F having a degree of oxidation of 1 to 22.

When the polysaccharide of Streptococcus pneumoniae serotype 17F is oxidized by adding 0.01 to 0.22 μg of periodate per 1 μg of the sugar content and is conjugated with a protein, the molecular weight of the conjugate may be 300 to 4,500 kDa, and the distribution of the molecular weight may be 15~60% (0.3 kd or less), and the polysaccharide/protein ratio may be 0.5 to 18.

One example of the present invention may provide an immunogenic composition comprising the immunogenic conjugate and a physiological acceptable vehicle.

Other example of the present invention may provide a vaccine comprising the immunogenic composition.

Other example of the present invention may provide a preparation method of an immunogenic conjugate of Streptococcus pneumoniae serotype 17F, comprising (a) a step of fermenting and dissolving a bacterial cell producing a Streptococcus pneumoniae serotype 17F capsular polysaccharide;

(b) a step of purifying the Streptococcus pneumoniae serotype 17F capsular polysaccharide in the dissolved cell;

(c) a step of hydrolyzing the purified Streptococcus pneumoniae serotype 17F capsular polysaccharide to size the polysaccharide;

(d) a step of reacting the sized polysaccharide of the (c) step to activate the polysaccharide; and (e) a step of combining the activated polysaccharide with a carrier protein to form a conjugate of Streptococcus pneumoniae serotype 17F capsular polysaccharide bound to the carrier protein.

A preparation method of an immunogenic conjugate of Streptococcus pneumoniae serotype 17F, characterized by that the carrier protein combined of the (e) step may form a conjugate with the activated polysaccharide by reacting it with a reducing agent, may be provided.

The (d) step may comprise a process of reacting 0.01~0.22 μg of periodate per 1 μg polysaccharide at a temperature of 20 to 25° C. for 15 to 20 hours.

The activated polysaccharide to be combined with the carrier protein of the (e) step may have a molecular weight of 400 to 900 kDa.

The immunogenic conjugate may have a molecular weight of 300 to 4,500 kDa.

The initial input ratio of the activated serotype 17F capsular polysaccharide versus the carrier protein (carrier protein:polysaccharide) may be 1:1.

In one example, at least 15 to 60% of the immunogenic conjugate molecular weight may be present within 0.3 Kd in a CL-4B column.

One example of the present invention may provide an immunogenic conjugate obtained by the method. One example of the present invention may provide an immunogenic composition comprising an immunogenic conjugate obtained by the method and a physiologically acceptable vehicle. Other example may provide a vaccine comprising the immunogenic composition.

One example of the present invention provides an immunogenic conjugate of *Streptococcus pneumoniae* serotype 20, comprising a capsular polysaccharide of serotype 20, derived from of *Streptococcus pneumoniae*; and a carrier protein bound to the capsular polysaccharide.

The polysaccharide of serotype 20 may be activated and bind to the carrier protein at a molecular weight of 400 to 800 kDa to form a conjugate.

In one example of the present invention, the immunogenic conjugate may have a molecular weight of 1,000 to 4,000 kDa, and for example, the carrier protein may be $CRM_{197}$.

In one example of the present invention, the ratio of the serotype 20 capsular polysaccharide to the carrier protein in the immunogenic conjugate (W/W) may be 1 to 5.

70 to 90% of the immunogenic conjugate of serotype 20 may be present within 0.3 Kd in a CL-4B column. Another example provides an immunogenic conjugate of *Streptococcus pneumoniae* serotype 20 having a degree of oxidation of 4 to 16.

When the polysaccharide of *Streptococcus pneumoniae* serotype 20 is oxidized by adding 0.01 to 0.04 μg of periodate per 1 μg of the sugar content and is conjugated with a protein, the molecular weight of the conjugate may be 1,000 to 4,000 kDa, and the distribution of the molecular weight may be 70~90% (0.3 kd or less), and the polysaccharide/protein ratio may be 1 to 5.

One example of the present invention may provide an immunogenic composition comprising the immunogenic conjugate and a physiological acceptable vehicle.

Other example of the present invention may provide a vaccine comprising the immunogenic composition.

Other example of the present invention may provide a preparation method of an immunogenic conjugate of *Streptococcus pneumoniae* serotype 20, comprising (a) a step of fermenting and dissolving a bacterial cell producing a *Streptococcus pneumoniae* serotype 20 capsular polysaccharide;

(b) a step of purifying the *Streptococcus pneumoniae* serotype 20 capsular polysaccharide in the dissolved cell;

(c) a step of reacting the polysaccharide with an oxidizing agent to activate it; and (d) a step of combining the activated polysaccharide with a carrier protein to form a conjugate of *Streptococcus pneumoniae* serotype 20 capsular polysaccharide bound to the carrier protein.

The carrier protein combined of the (d) step may be reacted with a reducing agent to form a conjugate with the activated polysaccharide.

The (c) step may comprise a process of reacting 0.01~0.04 μg of periodate per 1 μg polysaccharide at a temperature of 20 to 25° C. for 15 to 20 hours.

The activated polysaccharide to be combined with the carrier protein of the (d) step may have a molecular weight of 400 to 800 kDa.

In one example of the present invention, the immunogenic conjugate of the present invention by the method may have a molecular weight of 1,000 to 4,000 kDa.

The initial input ratio of the activated serotype 20 capsular polysaccharide versus the carrier protein (carrier protein:polysaccharide) may be 1:1.

In one example, at least 70 to 90% of the immunogenic conjugate molecular weight may be present within 0.3 Kd in a CL-4B column.

One example of the present invention may provide an immunogenic conjugate obtained by the method.

One example may provide an immunogenic composition comprising an immunogenic conjugate obtained by the method and a physiologically acceptable vehicle.

Other example may provide a vaccine comprising the immunogenic composition.

Characteristics of Serotype 20 Polysaccharide-Carrier Protein Conjugate

In one embodiment, the conjugate may have a molecular weight of 1,300 to 4,300 kDa, or a molecular weight of 1,250 to 4,250 kDa, or a molecular weight of 1,200 to 4,200 kDa, or a molecular weight of 1,150 to 4,150 kDa, or a molecular weight of 1,100 to 4,100 kDa, or a molecular weight of 1,000 to 4,000 kDa. All integers within any of the above ranges are considered as the embodiment.

In the above molecular weight ranges, a conjugate having an excellent yield of the conjugate may be formed stably. In addition, the ratio of free sugar may be reduced. Furthermore, it may contribute to excellent immunogenicity in the above molecular weight ranges.

The immunogenic composition of the present invention is formulated by combining them after purifying respective polysaccharide-protein conjugates.

The polysaccharide-protein conjugate of serotypes of the present invention may be characterized by the ratio of the saccharide to the carrier protein (amount of polysaccharide/amount of protein) (weight/weight).

In some embodiments, the ratio of the saccharide to the carrier protein of each serotype among the polysaccharide-protein conjugate (w/w) may be 0.1 to 7, 0.2 to 7.5, 0.3 to 7, 0.4 to 6.5, 0.5 to 6, 0.6 to 6.5, 0.7 to 6, 0.8 to 5.8, 0.9 to 5.6, 0.95 to 5.3, or 1 to 5. For example, it may be about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5.

In another embodiment, the ratio of the saccharide to the carrier protein (w/w) may be 1 to 5, 1.2 to 4.5, or 1.3 to 4.

Preferably, the carrier protein may be CRM197.

When the ratio of the saccharide to the carrier protein is same as above, a conjugate having an excellent yield of the conjugate may be formed stably. In addition, the ratio of free sugar may be reduced. Moreover, in case of the above range, not only the immunogenicity is excellent, but also the conjugate may be maintained stably without interference of other serotypes.

The conjugate and immunogenic composition of the present invention may comprise a free saccharide which is not conjugated to the carrier protein covalently but is present in the polysaccharide-protein conjugate composition. The free saccharide may be non-covalently associated with the polysaccharide-protein conjugate (that is, it may be non-covalently bound or adsorbed to the polysaccharide-protein conjugate, or be encapsulated in the polysaccharide-protein conjugate or by the polysaccharide-protein conjugate).

In a preferable embodiment, the polysaccharide-protein conjugate comprises a polysaccharide of each free serotype less than about 70%, about 60%, about 50%, 45%, 40%, 35%, 30%, 25%, 20%, 15%, or 10% to the total amount of the polysaccharide of each serotype.

The polysaccharide-protein conjugate of each serotype may be also characterized by its molecular size distribution (Kd). Using a size exclusion chromatography medium (CL-4B, Cross-linked Agarose beads, 4%), the relative molecular size distribution of the conjugate may be measured. The molecular size distribution of the conjugate is profiled using the size exclusion chromatography (SEC) in a gravity feed column. Big molecules excluded from pores in the medium are eluted faster than small molecules. Using a fraction collector, the column eluates are collected. The fractions are tested by colorimetry by saccharide analysis. For measurement of Kd, the column is scaled to set fractions in which molecules are completely excluded (V0), (Kd=0) and fractions showing the maximum maintenance (Vi), (Kd=1). The fractions in which the specified sample characteristic is reached (Ve) is related to Kd by the equation Kd=(Ve−V0)/(Vi−V0).

In a preferable embodiment, at least 30% of the polysaccharide-protein conjugate of each serotype may be present within 0.3 Kd in a CL-4B column.

In a preferable embodiment, at least 95% of the polysaccharide-protein conjugate of each serotype may be present within 0.3 Kd in a CL-4B column. In a preferable embodiment, at least 45%, 50%, 55%, 60%, 65%, 70%, 75%, 80%, 85% or 90% of the polysaccharide-protein conjugate of each serotype may be present within 0.3 Kd in a CL-4B column. In a preferable embodiment, at least 60% of the polysaccharide-protein conjugate of each serotype may be present within 0.3 Kd in a CL-4B column. In a preferable embodiment, 50 to 90% of the polysaccharide-protein conjugate of each serotype may be present within 0.3 Kd in a CL-4B column. In a preferable embodiment, 65 to 90% of the polysaccharide-protein conjugate of each serotype may be present within 0.3 Kd in a CL-4B column. In a preferable embodiment, 70 to 90% of the polysaccharide-protein conjugate of each serotype may be present within 0.3 Kd in a CL-4B column.

1.4 Combination of Capsular Saccharide-Carrier Protein

In one embodiment, the immunogenic composition of the present invention comprises a conjugate of one or more polysaccharide selected from the group consisting of *Streptococcus pneumoniae* serotypes 2, 9N, 17F and 20 and a protein. In one embodiment, any one of the immunogenic compositions may comprise a conjugate in which a polysaccharide derived from one or more selected from the group consisting of 1, 3, 4, 5, 6A, 6B, 7F, 8, 9V, 10A, 11A, 12F, 14, 15B, 18C, 19A, 19F, 22F, 23F, and 33F is further conjugated to the carrier protein.

In one embodiment, any one of the polysaccharide-protein conjugates among the immunogenic composition is conjugated to CRM197 and/or TT, respectively. Preferably, a 23-valent or 24-valent immunogenic composition may comprise both CRM197 and TT as the carrier protein, and in this case, preferably, serotype 5 comprises TT as the carrier protein. In one example, in the 23-valent immunogenic composition, the polysaccharides derived from serotype 3 and 5 are conjugated to TT, and polysaccharides derived from serotypes 1, 2, 6A, 6B, 7F, 8, 9N, 9V, 10A, 11A, 12F, 14, 15B, 17F, 18C, 19A, 19F, 20, 22F, 23F, and 33F are conjugated to CRM197. In one example, in the 24-valent immunogenic composition, the polysaccharides derived from serotypes 1 and 5 are conjugated to TT, and serotypes 2, 3, 4, 6A, 6B, 7F, 8, 9N, 9V, 10A, 11A, 12F, 14, 15B, 17F, 18C, 19A, 19F, 20, 22F, 23F, and 33F are conjugated to CRM197.

In one embodiment, the immunogenic composition may comprise a polysaccharide-protein conjugate derived from 1, 2, 3, 4, 5, 6, 7, 8, 9, 10, 11, 12, 13, 14, 15, 16, 17, 18, 19, 20, 21, 22, 23, or 24 different serotypes.

2. Dose of Immunogenic Composition

The amount of the capsular saccharide-carrier protein conjugate(s) among each dose is selected as the amount of inducing an immune protection response without significant side effects among typical vaccines. The amount as above may change depending on how a specific immunogen is used and how it is provided.

2.1 Amount of Capsular Polysaccharide-Carrier Protein Conjugate

The amount of the specific capsular polysaccharide-carrier protein in the immunogenic composition may be calculated on the basis of the total polysaccharides to the conjugate (conjugated and unconjugated). For example, the capsular polysaccharide-carrier protein conjugate having 20% free polysaccharides means having about 80 µg conjugated polysaccharides and about 20 µg unconjugated polysaccharides in 100 µg polysaccharide dose. The amount of the polysaccharide-protein conjugate may change depending on the pneumococcal serotypes. The polysaccharide concentration may be measured by anthrone or uronic acid analysis.

The "immunogenic amount" of the different polysaccharide components in the immunogenic composition may vary, and it may comprise any specific polysaccharide antigen of about 1 µg, about 2 µg, about 3 µg, about 4 µg, about 5 µg, about 6 µg, about 7 µg, about 8 µg, about 9 µg, about 10 µg, about 15 µg, about 20 µg, about 30 µg, about 40 µg, about 50 µg, about 60 µg, about 70 µg, about 80 µg, about 90 µg, or about 100 µg, respectively.

In general, each dose may comprise polysaccharides of 0.1 µg to 100 µg, particularly, 0.5 µg to 20 µg, more particularly, 1.0 µg to 10 µg, and more particularly 2.0 µg to 5.0 µg to the given serotype. All integers within any of the above ranges are considered as the embodiment.

In one embodiment, each dose may comprise polysaccharides of about 1.0 µg, about 1.2 µg, about 1.4 µg, about 1.6 µg, about 1.8 µg, about 2.0 µg, about 2.2 µg, about 2.4 µg, about 2.6 µg, about 2.8 µg, about 3.0 µg, about 3.2 µg, about 3.4 µg, about 3.6 µg, about 3.8 µg, about 4.0 µg, about 4.2 µg, about 4.4 µg, about 4.6 µg, about 4.8 µg, about 5.0 µg, about 5.2 µg, about 5.4 µg, about 5.6 µg, about 5.8 µg or about 6.0 µg to each specific capsular saccharide-carrier protein conjugate.

In one embodiment, each dose may comprise polysaccharides of 1 to 3 µg to the polysaccharide-protein derived from *Streptococcus pneumoniae* serotypes 1, 2, 3, 4, 5, 6A, 7F, 8, 9N, 9V, 10A, 11A, 12F, 14, 15B, 17F, 18C, 19A, 19F, 20, 22F, 23F and/or 33F. For example, it may comprise polysaccharides of about 1.1 µg, about 1.2 µg, about 1.3 µg, about 1.4 µg, about 1.5 µg, about 1.6 µg, about 1.7 µg, about 1.8 µg, about 1.9 µg, about 2.0 µg, about 2.1 µg, about 2.2 µg, about 2.3 µg, about 2.4 µg, about 2.5 µg, about 2.6 µg, about 2.7 µg, about 2.8 µg, about 2.9 µg, or about 3.0 µg.

In one embodiment, in case of further comprising a polysaccharide-protein conjugate derived from serotype 6B, polysaccharides of 2 to 6 µg may be comprised.

2.2 Amount of Carrier Protein

In one embodiment, the carrier protein may be CRM197 and/or TT.

In one embodiment, when the carrier protein is CRM197, each dose of the carrier protein comprised in the immunogenic composition may comprise carrier proteins of 10 µg to 150 µg, 20 µg to 100 µg, 25 µg to 95 µg. For example, the 24-valent immunogenic composition according to one embodiment of the present invention may comprise carrier proteins of 70 to 90 µg.

In one embodiment, when the carrier protein is TT, each dose of the carrier protein comprised in the immunogenic composition may comprise carrier proteins of 5 μg to 15 μg, 8 μg to 10 μg.

3. Adjuvant

In some embodiments, the immunogenic composition disclosed in the present invention may further comprise one or more adjuvants. The term "adjuvant" refers to a compound or mixture which increases an immune response against an antigen. The adjuvant may enhance an immune response against an antigen exhibiting weak immunogenicity and/or, may increase an antibody titer against an antigen and/or, may reduce an effective dose of an antigen for achieving an immune response in a subject, in case of single administration, as inducing no or weak antibody titer or cell mediated immune response. Thus, the adjuvant mostly plays a role of increasing an immune response, and this is known to those skilled in the art. The suitable adjuvant enhancing the efficacy of a composition includes the followings, but it is not limited thereto:

In one example, the adjuvant may include aluminum salts (alum), for example, aluminum hydroxide, aluminum phosphate, aluminum sulfate, and the like.

In a specific embodiment, the adjuvant is an aluminum salt. The aluminum salt adjuvant may be an alum-precipitated vaccine or an alum-adsorbed vaccine. The aluminum salt adjuvant is known in the art. The aluminum salt includes hydrated alumina, alumina hydrate, alumina trihydrate (ATH), aluminum hydrate, aluminum trihydrate, Alhydrogel, Superfos, Amphogel, aluminum hydroxide (III), aluminum hydroxyphosphate sulfate (aluminum phosphate adjuvant (APA)), amorphous alumina, trihydrated alumina, or trihydroxyaluminum, but not limited thereto.

APA is an aqueous suspension of aluminum hydroxyphosphate. APA is prepared by blending aluminum chloride and sodium phosphate at a volume ratio of 1:1 and precipitating aluminum hydroxyphosphate. After the blending process, by reducing in a size of a material using a high shear mixer, target aggregate particles having a size in a range of 2~8 μm are obtained. Subsequently, products are diafiltrated for saline solution and are steam sterilized.

In a specific embodiment, a protein is adsorbed at a ratio of 50-200 g protein/mg aluminum hydroxide using a commercially available Al(OH)3 (for example, Alhydrogel or Superfos of Denmark/Accurate Chemical and Scientific Co. (U.S. New York Westbury). In another embodiment, the adsorption of the protein differs depending on pI (isoelectric pH) of the protein and pH of a medium. The protein having lower pI are adsorbed to positively charged aluminum ion more strongly than the protein having higher pI. The aluminum salt may establish Ag depot slowly released over 2-3 weeks, and/or may involve in non-specific activation of macrophage and complement activation, and/or may stimulate a congenital immune mechanism (possibly through uric acid stimulation).

In a preferable embodiment, the adjuvant is an aluminum-based adjuvant selected from the group consisting of aluminum phosphate, aluminum sulfate and aluminum hydroxide. In one embodiment, the immunogenic composition disclosed herein comprises an aluminum phosphate adjuvant.

4. Formulation

The immunogenic composition of the present invention may be formulated in a liquid form (that is, solution or suspension) or in a lyophilized form. Advantageously, the liquid formulation may be directly administered in its packaged form, and therefore the formulation is ideal for injection without re-composition in an aqueous medium as required for the lyophilized composition of the present invention.

The formulation of the immunogenic composition of the present invention may be carried out using a method approved in the art. For example, the composition may be prepared by formulating an individual pneumococcal conjugate with a physiologically acceptable vehicle. The example of the vehicle as above unlimitedly includes water, buffered saline, polyol (for example, glycerol, propylene glycol, liquid polyethylene glycol) and dextrose solution.

The present invention provides an immunogenic composition comprising any one of combinations of the polysaccharide-protein conjugates disclosed and a pharmaceutically acceptable excipient, carrier or diluent.

In one embodiment, the immunogenic composition of the present invention is in a liquid form, preferably in an aqueous liquid form.

The immunogenic composition of the present invention may comprise one or more kinds among buffer, salt, divalent cation, non-ionic detergent, cryoprotectant, e.g. sugar, and anti-oxidant, e.g. free radical scavenger and chelating agent, and any of various combinations thereof.

In one embodiment, the immunogenic composition of the present invention comprises a buffer. In one embodiment, the buffer has pKa of about 3.5 to about 7.5. In some embodiments, the buffer is phosphate, succinate, histidine or citrate. In some embodiments, the buffer is succinate at a final concentration of 1 mM to 10 mM. In one specific embodiment, the final concentration of succinate is about 5 mM.

In one embodiment, the immunogenic composition of the present invention comprises a salt. In some embodiments, the salt is selected from the group consisting of magnesium chloride, potassium chloride, sodium chloride and combinations thereof. In a preferable embodiment, the salt is sodium chloride. In one specific embodiment, the immunogenic composition of the present invention comprises sodium chloride of 150 mM.

In one embodiment, the immunogenic composition of the present invention comprises a surfactant. The surfactant is selected from the group consisting of polyoxyethylene sorbitan fatty acid ester, polysorbate-80 (Tween 80), polysorbate-60 (Tween 60), polysorbate-40 (Tween 40) and polysorbate-20 (Tween 20), polyoxyethylene alkyl ether (including Brij 58, Brij 35, but not limited thereto), as well as other materials, for example, one or more kinds of non-ionic surfactants which include Triton X-100; Triton X-114, NP40, Span 85 and pluronic series of non-ionic surfactants (for example, pluronic 121), but not limited thereto. In a preferable embodiment, the immunogenic composition comprises polysorbate-80 or polysorbate-20, preferably polysorbate-20. In a preferable embodiment, the immunogenic composition comprises polysorbate-20 at a concentration of about 0.001% to about 2% (less than about 0.005% is preferable).

In one embodiment, the container of the present invention is prepared by glass, metal (for example, steel, stainless steel, aluminum, etc.) and/or polymers (for example, thermoplastic materials, elastomers, thermoplastic-elastomers). In one embodiment, the container of the present invention is prepared by glass.

In one embodiment, the present invention provides an injection filled with any one of the immunogenic compositions disclosed in the present invention. In one specific embodiment, the injection is treated with silicon and/or is prepared by glass.

5. Use

In one embodiment, the immunogenic composition disclosed in the present invention is to be used as a pharmaceutical. The amount of the conjugate in the composition is selected as an amount of inducing an immune protective response without significant side effects. Such an amount may vary depending on serotypes of pneumococcus.

The immunogenic composition disclosed in the present invention may be used by various therapeutic or prophylactic methods for prevention, treatment or improvement of bacterial infection, diseases or conditions in a subject. In particular, the immunogenic composition disclosed in the present invention may be used for prevention, treatment or improvement of Streptococcus pneumoniae infection, diseases or conditions in a subject.

All references or patent applications cited in the present patent specification are incorporated by reference herein.

The present invention is illustrated by accompanying examples. The following examples are conducted by using common standard techniques known to those skilled in the art, except where otherwise specifically described. These examples are illustrative, but does not limit the present invention.

The immunogenic composition disclosed in the present invention may be used by various therapeutic or prophylactic methods for prevention, treatment or improvement of bacterial infection, diseases or conditions in a subject. In particular, the immunogenic composition disclosed in the present invention may be used for prevention, treatment or improvement of Streptococcus pneumoniae infection, diseases or conditions in a subject.

In one embodiment, the present invention provides a method for preventing, treating or improving Streptococcus pneumoniae infection, diseases or conditions in a subject, comprising administering an immunologically effective dose of the immunogenic composition of the present invention into the subject.

In some embodiments as above, the infection, diseases or conditions are selected from the group consisting of pneumonia, sinusitis, otitis media, acute otitis media, cerebromeningitis, bacteriemia, septicemia, pyothorax, conjunctivitis, osteomyelitis, septic arthritis, endocarditis, peritonitis, pericarditis, mastoiditis, cellulitis, soft tissue infection and brain abscess.

In one embodiment, the present invention provides a method of inducing an immune response against Streptococcus pneumoniae in a subject, comprising administering an immunologically effective dose of immunogenic composition of the present invention into the subject.

In one embodiment, the immunogenic composition disclosed in the present invention is to be used as a vaccine. In an embodiment as above, the immunogenic composition disclosed in the present invention may be used for preventing Streptococcus pneumoniae infection. Thus, in one embodiment, the present invention provides a method for preventing infection by Streptococcus pneumoniae in a subject, comprising administering an immunologically effective dose of the immunogenic composition of the present invention into the subject.

In some embodiments as above, the infection is selected from the group consisting of pneumonia, sinusitis, otitis media, acute otitis media, cerebromeningitis, bacteriemia, septicemia, pyothorax, conjunctivitis, osteomyelitis, septic arthritis, endocarditis, peritonitis, pericarditis, mastoiditis, cellulitis, soft tissue infection and brain abscess. In one embodiment, the subject to be vaccinated is a mammal, for example, human, cat, sheep, pig, horse, cow or dog.

In one embodiment, the immunogenic composition disclosed in the present invention is to be used for a method for prevention, treatment or improvement of infection, diseases or conditions related to Streptococcus pneumoniae in a subject. In some embodiments as above, the infection, diseases or conditions are selected from the group consisting of pneumonia, sinusitis, otitis media, acute otitis media, cerebromeningitis, bacteriemia, septicemia, pyothorax, conjunctivitis, osteomyelitis, septic arthritis, endocarditis, peritonitis, pericarditis, mastoiditis, cellulitis, soft tissue infection and brain abscess.

In one embodiment, the immunogenic composition disclosed in the present invention to be used as a vaccine. In an embodiment as above, the immunogenic composition disclosed in the present invention may be used for Streptococcus pneumoniae preventing infection in a subject. Thus, in one embodiment, the immunogenic composition disclosed in the present invention is to be used for a prophylactic method of infection by Streptococcus pneumoniae in a subject. In some embodiments as above, the infection is selected from the group consisting of pneumonia, sinusitis, otitis media, acute otitis media, cerebromeningitis, bacteriemia, septicemia, pyothorax, conjunctivitis, osteomyelitis, septic arthritis, endocarditis, peritonitis, pericarditis, mastoiditis, cellulitis, soft tissue infection and brain abscess. In one embodiment, the subject to be vaccinated is a mammal, for example, human, cat, sheep, pig, horse, cow or dog.

The immunogenic composition of the present invention may be used for protecting or treating human sensitive to pneumococcal infection by administering the immunogenic composition through a systemic or mucosal route. In one embodiment, the immunogenic composition disclosed in the present invention is administered through an intramuscular, intraperitoneal, intracutaneous or subcutaneous route. In one embodiment, the immunogenic composition disclosed in the present invention is administered by intramuscular, intraperitoneal, intracutaneous or subcutaneous injection. In one embodiment, the immunogenic composition disclosed in the present invention is administered by intramuscular or subcutaneous injection.

In the ELISA (enzyme-linked immunosorbent assay) method, an antibody from serum of the vaccinated subject is cultured with a polysaccharide adsorbed to a solid support. The bound antibody is detected by using an enzyme-conjugated secondary detection antibody.

The ELISA measures a type-specific IgG anti-Streptococcus pneumoniae capsular polysaccharide (PS) antibody present in human serum. When the dilution of human serum is added to a type-specific capsule PS-coated microtitration plate, the antibody specific to the capsule PS binds to the microtitration plate. The antibody bound to the plate is detected by using a goat anti-human IgG alkaline phosphatase-labeled antibody, followed by a p-nitrophenyl phosphate substrate.

The optical density of the colored final product is proportional to the amount of the anti-capsule PS antibody present in the serum.

In one embodiment, the immunogenic composition comprising one or more of polysaccharide-protein conjugates from Streptococcus pneumoniae serotypes 2, 9N, 17F and 20 may induce an IgG antibody capable of binding to the Streptococcus pneumoniae serotype 15B polysaccharide at a concentration of at least 0.05, 0.1, 0.2, 0.3, 0.35, 0.4 or 0.5 µg/ml, as measured by ELISA analysis in human.

In one embodiment, the immunogenic composition comprising one or more of polysaccharide-protein conjugates from Streptococcus pneumoniae serotypes 2, 9N, 17F and 20 may induce formation of an antibody capable of phagocytosis of *Streptococcus pneumoniae* of one or more serotype selected from *Streptococcus pneumoniae* serotypes 2, 9N, 17F and 20 in the phagocytosis analysis initiated by opsonin as disclosed in the present invention.

In one embodiment, the immunogenic composition comprising one or more polysaccharide-protein conjugates from *Streptococcus pneumoniae* serotypes 2, 9N, 17F and 20 has a bigger OPA titer than an OPA titer obtained for a natural *Streptococcus pneumoniae* capsular polysaccharide which is not conjugated during the test in the OPA analysis.

The pneumococcus opsonin-initiated phagocytosis analysis (OPA) measuring killing of *Streptococcus pneumoniae* cells by cells having a phagocytosis effect under the present of a functional antibody and a complement is considered as an important substitute in evaluating the efficacy of a pneumococcal vaccine.

The opsonin-initiated phagocytosis analysis (OPA) may be performed by culturing the mixture of *Streptococcus pneumoniae* cells, heat-inactivated human serum to be tested, differentiated HL-6 cells (phagocytes) and exogenous complement sources of supply (for example, baby rabbit complement) together. The opsonin-initiated phagocytosis is progressed during the culturing, and bacterial cells coated with an antibody and a complement are killed during the opsonin-initiated phagocytosis. The colony forming unit (cfu) of survived bacteria escaping from the opsonin-initiated phagocytosis is measured by painting out the analysis mixture. The OPA titer is defined as mutual dilution producing 50% reduction of the number of bacteria in a control well without test serum. The OPA titer is interpolated from 2 diluents comprising the 50% killing cutoff.

The terminal titer of 1:8 or more is considered as the result of the amount in the killing type OPA.

In one embodiment, the immunogenic composition comprising one or more polysaccharide-protein conjugates from *Streptococcus pneumoniae* serotypes 2, 9N, 17F and 20 may induce at least 1:8 titer against one or more serotypes selected from *Streptococcus pneumoniae* serotypes 2, 9N, 17F and 20, as measured by the opsonin-initiated phagocytosis killing analysis (OPA). In one embodiment, the immunogenic composition comprising one or more polysaccharide-protein conjugates from *Streptococcus pneumoniae* serotypes 2, 9N, 17F and 20 may induce at least 1:8 titer against *Streptococcus pneumoniae* serotypes 2, 9N, 17F and 20 in at least 60%, 70%, 80%, 90% or at least 93% of the subject, as measured by the opsonin-initiated phagocytosis killing analysis (OPA).

6. Subject to be Treated by the Immunogenic Composition of the Present Invention As disclosed in the present invention, the immunogenic composition disclosed in the present invention may be used for various therapeutic or prophylactic methods for preventing, treating or improving bacterial infection, diseases or conditions in a subject.

In a preferable embodiment, the subject is human. In the most preferable embodiment, the subject is newborn babies (that is, 3 months or less), infants (that is, 3 months to 1 year), or toddlers (that is, 1 year to 4 years).

In one embodiment, the immunogenic composition disclosed in the present invention is to be used as a vaccine. In the embodiment as above, the subject to be vaccinated may be less than 1 year. For example, the subject to be vaccinated may have an age of about 1, about 2, about 3, about 4, about 5, about 6, about 7, about 8, about 9, about 10, about 11 or about 12 months. In one embodiment, the subject to be vaccinated is about 2, about 4 or about 6 months. In another embodiment, the subject to be vaccinated is less than 2 years. For example, the subject to be vaccinated has an age of about 12 months to about 15 months. In some cases, one dose of the immunogenic composition according to the present invention may be required, but in some circumstances, a second, third or fourth dose may be provided.

In an embodiment of the present invention, the subject to be vaccinated is an adult over 50 years old, more preferably, an adult over 55 years old.

In one embodiment, the subject to be vaccinated is an adult over 65 years old, 70 years old, 75 years old, or 80 years old.

In one embodiment, the subject to be vaccinated is an immune-deficient individual, in particular, human. The immune-deficient individual is generally defined as people with reduced or decreased ability to initiate normal body fluids or cell defense against attacks by infectious agents.

In one embodiment of the present invention, the immune-deficient subject to be vaccinated suffers from diseases or conditions damaging the immune system and produces an antibody response insufficient for protecting from pneumococcal disease or treating the diseases.

In one embodiment, the diseases are primary immunodeficiency diseases. Preferably, the primary immunodeficiency diseases are selected from the group consisting of complex T- and B-cells immunodeficiency, antibody deficiency, well defined syndrome, immunodysregulation disease, phagocyte disease, congenital deficiency, autoinflammatory disease and complement deficiency.

In a specific embodiment of the present invention, the immune-deficient subject to be vaccinated may suffer from a disease selected from the group consisting of the followings: HIV-infection, acquired immune deficiency syndrome (AIDS), cancer, chronic heart or lung disease, congestive heart failure, diabetes, chronic liver disease, alcohol abuse, cirrhosis, spinal fluid leak, cardiomyopathy, chronic bronchitis, emphysema, chronic obstructive pulmonary disease (COPD), spleen dysfunction (for example, sickle cell disease), spleen function deficiency (alienia), hematologic malignancy, leukemia, multiple myeloma, Hodgkin disease, lymphoma, renal insufficiency, nephrotic syndrome and asthma.

In one embodiment of the present invention, the immune-deficient subject to be vaccinated may suffer from malnutrition.

In a specific embodiment of the present invention, the immune-deficient subject to be vaccinated may be on medication or treatment that reduces the body's resistance to infection.

In a specific embodiment of the present invention, the immune-deficient subject to be vaccinated may be a smoker.

In a specific embodiment of the present invention, the immune-deficient subject to be vaccinated may have the number of white blood cells (leukocytes number) of $5 \times 10^9$ cell/liter or less, or $4 \times 10^9$ cell/liter or less, or $3 \times 10^9$ cell/liter or less, or $2 \times 10^9$ cell/liter or less, or $1 \times 10^9$ cell/liter or less, or $0.5 \times 10^9$ cell/liter or less, or $0.3 \times 10^9$ cell/liter or less, or $0.1 \times 10^9$ cell/liter or less.

The number of white blood cells (leukocytes number): the number of white blood cells (WBC) in blood. The WBC is measured as a part of CBC (complete blood cell number). The white blood cells are infection-struggling cells and are different from red (oxygen-delivery) blood cells as red blood cells.

There are different types of white blood cells, for example, neutrophils (polymorphous nucleus white blood cell; PMN), stab cells (some immature neutrophils), T-type lymphocytes (T-cell), B-type lymphocytes (B-cell), monocytes, eosinophils and basophils. All the above types of white blood cells are reflected to the number of white blood cells. The normal range of the white blood cells is mostly 4,300 to 10,800 cell/blood cubic milliliter. This is also referred as the number of white blood cells, and it may be represented by the international unit as 4.3 to $10.8 \times 10^9$/liter.

In a specific embodiment of the present invention, the immune-deficient subject to be vaccinated is suffering from neutropenia. In a specific embodiment of the present invention, the immune-deficient subject to be vaccinated may have the number of neutrophils of $2 \times 10^9$ cell/liter or less, or $1 \times 10^9$ cell/liter or less, or $0.5 \times 10^9$ cell/liter or less, or $0.1 \times 10^9$ cell/liter or less, or $0.05 \times 10^9$ cell/liter or less.

The low number of white blood cells or "neutropenia" is a condition characterized by abnormally low level of neutrophils in circulating blood. The neutrophil is a unique kind of white blood cells, which helps prevent infection and struggle infection. The most common reason why cancer patients suffer from neutropenia is as side effects of chemotherapy. The chemotherapy-caused neutropenia increases infection riskiness of patients and halts cancer treatment.

In a specific embodiment of the present invention, the immune-deficient subject to be vaccinated may have a CD4+ cell number of 500/mm$^3$ or less, or a CD4+ cell number of 300/mm$^3$ or less, or a CD4+ cell number of 200/mm$^3$ or less, or a CD4+ cell number of 100/mm$^3$ or less, or a CD4+ cell number of 75/mm$^3$ or less, or a CD4+ cell number of 50/mm$^3$ or less.

The CD4 cell test is commonly reported as the cell number of mm$^3$. The normal CD4 number is 500 to 1,600, and the CD8 number is 375 to 1,100. The CD4 number falls significantly in people with HIV.

In one embodiment of the present invention, any subject of the immune-deficient subject disclosed in the present invention may be a human male or human female.

7. Prescribed Diet

In some cases, one dose of the immunogenic composition according to the present invention may be required, but in some circumstances, for example, under the condition of greater immune-deficiency, a second, third or fourth dose may be provided. Following the initial vaccination, the subject may receive one or more additional immunizations at appropriate intervals.

In one embodiment, the vaccination schedule of the immunogenic composition according to the present invention is a single dose. In a specific embodiment, the single dose schedule is for a healthy human of at least 2 years.

In one embodiment, the vaccination schedule of the immunogenic composition according to the present invention is a multiple dose schedule. In a specific embodiment, the multiple dose schedule consists of a series of 2 doses separated by an interval of about one month to about two months. In a specific embodiment, the multiple dose schedule consists of a series of 2 doses separated by an interval of about 1 month, or a series of 2 doses separated by an interval of about 2 months.

In another embodiment, the multiple dose schedule consists of a series of 3 doses separated by an interval of about 1 month to about 2 months. In other embodiment, the multiple dose schedule consists of a series of 3 doses separated by an interval of about 1 month, or a series of 3 doses separated by an interval of about 2 months.

In other embodiment, the multiple dose schedule consists of a series of 3 doses separated by an interval of about 1 month to about 2 months and subsequent fourth dose of about 10 months to about 13 months after the first dose. In other embodiment, the multiple dose schedule consists of a series of 3 doses separated by an interval of about 1 month and subsequent fourth dose of about 10 months to about 13 months after the first dose, or a series of 3 doses separated by an interval of about 2 months and subsequent fourth dose of about 10 months to about 13 months after the first dose.

In one embodiment, the multiple dose schedule consists of at least 1 dose (for example, 1, 2 or 3 doses) at 1 year and subsequent at least 1 dose of toddler dose.

In one embodiment, the multiple dose schedule consists of a series of 2 or 3 doses separated by an interval of about 1 month to about 2 months (for example, 28 to 56 days between doses) after starting at 2 months, and a subsequent toddler dose of 12 to 18 months. In one embodiment, the multiple dose schedule consists of a series of 3 doses separated by an interval of about 1 month to about 2 months (for example, 28 to 56 days between doses) after starting at 2 months, and a subsequent toddler dose of 12 to 15 months. In other embodiment, the multiple dose schedule consists of a series of 2 doses separated by an interval of about 2 months after starting at 2 months, and a subsequent toddler dose of 12 to 18 months.

In one embodiment, the multiple dose schedule consists of a series of 4 vaccine doses at 2, 4, 6 and 12 to 15 months.

In one embodiment, the initial dose is provided at 0 day, and once or more of additional doses are provided at an interval of about 2 to about 24 weeks, preferably, at an administration interval of 4 to 8 weeks.

In one embodiment, the initial dose is provided at o day, the additional dose is provided about 3 months later.

Advantageous Effects

The present invention can provide an immunogenic conjugate for a new serotype such as serotype 17F which has not provided a protection range previously.

The present invention can provide a multivalent pneumococcal vaccine capable of providing a wide range of protection by comprising a new serotype conjugate which has not provided a protection range previously.

In addition, it is possible to form an antibody against various pneumococcal serotypes without any special interference phenomenon, thereby providing a wide spectrum of immunity.

The present invention can provide excellent antibody titer.

The multivalent pneumococcal vaccine of the present invention exhibits less side effects.

The vaccine of the present invention can be inoculated to infants and toddlers and can be inoculated to the elderly.

MODE FOR INVENTION

Hereinafter, the present invention will be described with reference to the following examples and the like in order to describe it more specifically. However, the examples according to the present invention may be modified into various other forms, and the scope of the present invention should not be construed as being limited to the examples described below. The examples of the present invention are provided to illustrate the present invention in order to facilitate a specific understanding of the present invention.

EXAMPLE 1. PREPARATION OF SEROTYPE 2, 9N, 17F or 20-DERIVED POLYSACCHARIDE-PROTEIN CONJUGATE VACCINE

[1. *Streptococcus pneumoniae* Serotype 2-Derived Polysaccharide-Protein Conjugate]

Preparation of Polysaccharide Protein Conjugate from *Streptococcus pneumoniae* Serotype 2

Preparation of Cell Bank for Master and Preparation

*Streptococcus pneumoniae* serotype 2 was acquired from American Type Culture Collection (ATCC) (strain ATCC 6302). In order to enhance the strain and remove components of animal origin, a seed stock was cultured for several generations. The seed vial was frozen with synthetic glycerol as a cryopreservative (<−70° C.). For preparation of cell bank, all cultures were proliferated in a soybean-based medium. Before freezing, cells were concentrated by centrifugation and the used medium was removed, and then a cell pellet was resuspended in a new medium containing a cryopreservative (e.g.: synthetic glycerol).

Fermentation

The cultures derived from the cell bank for preparation was used and inoculated into a seed bottle containing a soybean-based medium. Before satisfying the growth requirements, it was cultured at a certain temperature without stirring. Using the seed bottle, it was inoculated to a seed fermenter containing the soybean-based medium in which the temperature, pH and stirring speed were controlled. After the growth was stopped, or at the time of reaching the work capacity of the fermenter, fermentation was terminated. After terminating the fermentation process by adding an inactivator, cell residuals were removed using the combination of continuous flow centrifugation and filtration.

Purification

The purification of the pneumococcal polysaccharide was composed of multiple media filtration, several times of concentration/diafiltration work and precipitation/elution steps.

Activation

The final polysaccharide concentration was adjusted to be about 2.0 g/L in 0.01N hydrochloric acid solution by adding a calculated amount of 0.1N hydrochloric acid solution and WFI in order. For hydrolysis of the polysaccharide, the hydrolysis reaction was carried out at 60° C. for 60 minutes. After lowering the temperature of the reaction solution to the room temperature, the reaction pH was adjusted to approximately 6.0 by adding 0.1M sodium monohydrogen phosphate solution. After adjusting the pH, the temperature was adjusted to 23° C. The oxidation was initiated by adding sodium periodic acid of approximately 0.023~0.114 mg per 1 mg sugar. The oxidation reaction was carried out at 23° C. for 18 hours.

The concentration and diafiltration of the activated polysaccharide were performed using 100 kDa MWCO ultrafiltration membrane. Diafiltration was performed on WFI of 10-fold diafiltration volume. Then, the purified activated polysaccharide was stored at 2~8° C. The purified activated polysaccharide was characterized by in particular, (i) polysaccharide concentration by colorimetric determination, (ii) aldehyde concentration by colorimetric determination, (iii) degree of oxidation and (iv) molecular weight by SEC-MALLS.

SEC-MALLS is used for determining the molecular weights of the polysaccharide and polysaccharide-protein conjugate. SEC is used for separating the polysaccharide by fluid dynamical volume. The refractive index (RI) and multi-angle laser light scattering detector are used for molecular weight determination. When light interacts with a material, light is scattering and the amount of scattered light is related to concentration, square of do/dc (unique refractive index increase) and molar mass of a material. The molecular weight measured value is calculated on the basis of the reading value from scattered light signal from MALLS detector and the concentration signal from RI detector.

The degree of oxidation (DO) of the activated polysaccharide was determined by 'mole of sugar repeating unit mole of aldehyde'. By various colorimetry methods, for example, using Anthrone method, the mole of sugar repeating unit was determined. In addition, at the same time, using Park-Johnson colorimetry method, the mole of aldehyde was determined.

Preferably, the activated *Streptococcus pneumoniae* serotype 2 capsular polysaccharide obtained by the method has a degree of oxidation of 2 to 18 and a molecular weight of about 100 kDa to 400 kDa.

Conjugation Process

The activated polysaccharide was combined with sucrose at a ratio of sucrose of 2 to 8 g per the activated polysaccharide gram. Subsequently, the bottle of the combined mixture was lyophilized. Following lyophilization, the bottle containing the lyophilized activated polysaccharide was stored at −20 to −30° C. The calculated amount of CRM197 protein was separately lyophilized. The lyophilized CRM197 was stored at −20 to −30° C.

The lyophilized activated polysaccharide was recomposed in anhydrous dimethyl sulfoxide solution (DMSO). When completing dissolution of the polysaccharide, for recomposing anhydrous DMSO, it was added to lyophilized CRM197. The activated polysaccharide recomposed in the reaction container was combined with the recomposed CRM197 (input ratio 0.5 to 2:1) and then it was mixed thoroughly. The conjugation reaction was initiated by adding sodium cyanoborohydride (NaBH$_3$CN) of 1.0 mole equivalent to the reaction mixture. WFI was added to the reaction mixture at a target concentration of 1% (v/v) and it was reacted at 23° C. for 22 to 26 hours. The conjugation reaction was terminated by adding sodium borohydride (NaBH$_4$) of 2.0 mole equivalent and adding WFI at a target concentration of 5% (v/v) to the reaction mixture, thereby capping unreacted aldehyde. The capping reaction was conducted at 23° C. for 4.5 hours.

The conjugate solution was diluted with 0.9% sodium chloride solution during the preparation for purification by concentration and diafiltration using 100 kDa MWCO membrane. The diluted conjugate solution was passed through a 0.8 μm filter and diafiltration was carried out using 0.9% sodium chloride at a 15-fold to 40-fold diafiltration volume. After completing the diafiltration, the residual solution was filtrated through a 0.2 μm filter. The conjugate solution was diluted with 0.9% sodium chloride solution so as to be less than approximately 0.55 mg/mL concentration and was under sterile filtration and was stored at 2 to 8° C.

The purified serotype 2 conjugate was characterized by (i) polysaccharide concentration by colorimetric determination, (ii) protein concentration by colorimetric determination (Lowry), (iii) ratio of polysaccharides to protein, (iv) molecular size distribution by size exclusion chromatography (CL-4B), (iv) content of free sugar and (v) molecular weight by SEC-MALLS.

The characteristic change of the serotype 2 conjugate was observed by controlling the degree of oxidation (DO) based on the preparation method. The result was summarized in Table 1.

TABLE 1

| Conjugate number | 1-1 | 1-2 | 1-3 | 1-4 |
|---|---|---|---|---|
| Activated polysaccharide molecular weight, kDa | 365 | 313 | 300 | 231 |
| D0 | 14.2 | 8.6 | 6.7 | 2.7 |
| Input ratio (P:S) | | 1:1 | | |
| % Conjugate yield | 72 | 47 | 57 | 67 |
| Ratio of saccharides to protein | 1.2 | 1.1 | 1.2 | 1.0 |
| % Free polysaccharide | 27 | 13 | 8 | 1 |
| % Molecular weight distribution | 93 | 92 | 88 | 64 |
| Conjugate molecular weight, kDa | 4,918 | 3,845 | 3,485 | 1,988 |

The characteristic change of the serotype 2 conjugate was observed by controlling the mixing ratio of the activated polysaccharides and CRM197 during the lyophilization on the basis of the preparation method. The result was summarized in Table 2.

TABLE 2

| Conjugate number | 1-5 | 1-6 | 1-7 | 1-8 | 1-9 | 1-10 | 1-11 | 1-12 | 1-13 | 1-14 |
|---|---|---|---|---|---|---|---|---|---|---|
| Activated polysaccharide molecular weight, kDa | | | 260 | | | | | 147 | | |
| D0 | | | 9.4 | | | | | 3.0 | | |
| Input ratio (P:S) | 2:1 | 1.5:1 | 1:1 | 0.7:1 | 0.5:1 | 2:1 | 1.5:1 | 1:1 | 0.7:1 | 0.5:1 |
| % Conjugate yield | 47 | 53 | 57 | 58 | 58 | 64 | 70 | 70 | 73 | 68 |
| Ratio of saccharides to protein | 0.53 | 0.69 | 0.99 | 1.44 | 1.81 | 0.58 | 0.69 | 1.04 | 1.41 | 1.86 |
| % Free polysaccharide | 14 | 15 | 18 | 26 | 27 | 1 | 0 | 1 | 9 | 14 |
| % Molecular weight distribution | 94 | 96 | 97 | 96 | 94 | 76 | 71 | 67 | 65 | 63 |
| Conjugate molecular weight, kDa | 15,819 | 11,389 | 5,532 | 3,544 | 2,629 | 8,255 | 4,070 | 2,185 | 1,226 | 1,050 |

Research on Immunogenicity of Serotype 2 Polysaccharide-Protein Conjugate

A monovalent conjugate composition comprising a polysaccharide-protein conjugate from *Streptococcus pneumoniae* serotype 2 all individually conjugated to CRM197 was formulated.

The immunogenicity of the monovalent immunogenic composition of the Table 1 and Table 2 was analyzed using ELISA in a rabbit, thereby measuring a serotype-specific IgG concentration in serum.

5 female New Zealand white rabbit group of 2.5 kg to 3.5 kg was immunized via intramuscular route at the 0th week with the proposed human clinical dose (conjugate 2.2 μg; +aluminum 0.25 mg/10 as $AlPO_4$). The rabbit was further immunized at the 2nd week with the same dose of conjugate vaccine, and subsequently blood-gathering was carried out at the 4th week. The serotype-specific ELISA was performed in the 0th and 4th serum samples.

The analysis result was shown in Table 3. The rabbit immunized with the monovalent conjugate composition (conjugate number 1-6) exhibited a significant increase of the total IgG titer against serotype 2. In the rabbit immunized with other conjugate, a significant increase of the total IgG titer was shown.

The values of the following Table 3 are the result of showing the measured IgG concentration after immunizing with the conjugate number 1-6 of the Table 1.

TABLE 3

| | IgG concentration (U/mL) | |
|---|---|---|
| Serotype | Pre-immunization | Post-immunization |
| 2 | 130.0 | 62,164.7 |

[2. *Streptococcus pneumoniae* Serotype 9N-Derived Polysaccharide-Protein Conjugate]

Preparation of *Streptococcus pneumoniae* Serotype 9N-Derived Polysaccharide-Protein Conjugate Preparation of Cell Band for Master and Preparation

*Streptococcus pneumoniae* serotype 9N was obtained from American Type Culture Collection (ATCC) (strain ATCC 6309). It was progressed in the same manner as serotype 2.

Fermentation

It was progressed in the same manner as serotype 2.

Purification

It was progressed in the same manner as serotype 2.

Activation

The final polysaccharide concentration of about 2.0 g/L was provided by adding a calculated amount of WFI in order. If needed, the reaction pH was adjusted to approximately 6.0. After adjusting the pH, the reaction temperature was adjusted to 23° C. The oxidation was initiated by adding sodium periodic acid of 0.024~0.189 mg per approximately 1 mg sugar. The oxidation reaction was carried out at 23° C. for 18 hours.

The concentration and diafiltration of the activated polysaccharide were performed using 100 kDa MWCO ultrafiltration membrane. Diafiltration was performed on WFI of 10-fold diafiltration volume. Then, the purified activated polysaccharide was stored at 2~8° C. The purified activated polysaccharide was characterized by in particular, (i) polysaccharide concentration by colorimetric determination, (ii) aldehyde concentration by colorimetric determination, (iii) degree of oxidation and (iv) molecular weight by SEC-MALLS.

SEC-MALLS is used for determining the molecular weights of the polysaccharide and polysaccharide-protein conjugate. SEC is used for separating the polysaccharide by fluid dynamical volume. The refractive index (RI) and multi-angle laser light scattering detector are used for molecular weight determination. When light interacts with a material, light is scattering and the amount of scattered light is related to concentration, square of do/dc (unique refractive index increase) and molar mass of a material. The molecular weight measured value is calculated on the basis of the reading value from scattered light signal from MALLS detector and the concentration signal from RI detector.

The degree of oxidation (DO) of the activated polysaccharide was determined by 'mole of sugar repeating unit mole of aldehyde'. By various colorimetry methods, for example, using Anthrone method, the mole of sugar repeating unit was determined. In addition, at the same time, using Park-Johnson colorimetry method, the mole of aldehyde was determined.

Preferably, the activated *Streptococcus pneumoniae* serotype 9N capsular polysaccharide obtained by the method has a degree of oxidation of 2 to 19 and a molecular weight of about 200 kDa to 700 kDa.

Conjugation Process

The activated polysaccharide was combined with the carrier protein, CRM197 at a ratio of CRM197 of 0.5 to 2 grams per the activated polysaccharide gram. Subsequently, the combined mixture was lyophilized. Following lyophilization, the lyophilized mixture of the activated polysaccharide and CRM197 was stored at −20° C.

The lyophilized mixture of the activated polysaccharide and CRM197 was recomposed in 0.1M sodium phosphate solution and then was mixed sufficiently. The final polysaccharide concentration in the reaction solution is about 10 to 20 g/L. The conjugation was initiated by adding sodium cyanoborohydride (NaBH$_3$CN) of 1.2 mole equivalent to the mixture, and it was reacted at 37° C. for 48 hours. The conjugation reaction was terminated by adding 0.9% sodium chloride solution at the same volume as the conjugation reaction solution and then adding sodium borohydride (NaBH$_4$) of 2.0 mole equivalent, thereby capping unreacted aldehyde. The capping reaction was conducted at 23° C. for 4.5 hours.

The conjugate solution was diluted with 0.9% sodium chloride solution during the preparation for purification by concentration and diafiltration using 100 kDa MWCO membrane. The diluted conjugate solution was passed through a 0.45 μm filter and purification by concentration and diafiltration was carried out. Diafiltration using 100 kDa MWCO membrane was carried out using 0.9% sodium chloride solution at a 15-fold to 40-fold diafiltration volume. After completing the diafiltration, the residual solution was filtrated through a 0.2 μm filter. The conjugate solution was diluted so as to be less than approximately 0.55 mg/mL concentration and was under sterile filtration, and was stored at 2 to 8° C.

The purified serotype 9N conjugate was particularly characterized by (i) polysaccharide concentration by colorimetric determination, (ii) protein concentration by colorimetric determination (Lowry), (iii) ratio of polysaccharides to protein, (iv) molecular size distribution by size exclusion chromatography (CL-4B), (iv) content of free sugar and (v) molecular weight by SEC-MALLS.

The characteristic change of the serotype 9N conjugate was observed by controlling the degree of oxidation (DO) based on the preparation method. The result was summarized in Table 4.

TABLE 4

| Conjugate number | 2-1 | 2-2 | 2-3 | 2-4 | 2-5 | 2-6 |
|---|---|---|---|---|---|---|
| Activated polysaccharide molecular weight, kDa | 582 | 619 | 459 | 563 | 490 | 427 |
| DO | 18.2 | 9.4 | 7.4 | 6.7 | 4.3 | 2.3 |
| Input ratio (P:S) | | | 0.8:1 | | | |
| Polysaccharide concentration in conjugation reaction solution, g/L | | | 20.0 | | | |
| % Conjugate yield | 53 | 43 | 39 | 32 | 33 | 39 |
| Ratio of saccharides to protein | 2.1 | 1.5 | 1.3 | 1.1 | 1.0 | 0.78 |
| % Free polysaccharide | 44 | 28 | 22 | 20 | 21 | 31 |
| % Molecular weight distribution | 52 | 49 | 50 | 55 | 44 | 31 |
| Conjugate molecular weight, kDa | 860 | 1,110 | 1,912 | 1,168 | 1,189 | 1,160 |

The characteristic change of the serotype 9N conjugate was observed by controlling the mixing ratio of the activated polysaccharides and CRM197 during the lyophilization on the basis of the preparation method. The result was summarized in Table 5.

TABLE 5

| Conjugate number | 2-7 | 2-8 | 2-9 | 2-10 | 2-11 |
|---|---|---|---|---|---|
| Activated polysaccharide molecular weight, kDa | | | 287 | | |
| DO | | | 5.6 | | |
| Input ratio (P:S) | 2:1 | 1.5:1 | 1:1 | 0.67:1 | 0.5:1 |
| Polysaccharide concentration in conjugation reaction solution, g/L | | | 20.0 | | |
| % Conjugate yield | 25 | 50 | 43 | 41 | 66 |
| Ratio of saccharides to protein | 0.71 | 0.85 | 1.0 | 1.2 | 1.8 |
| % Free polysaccharide | 5 | 6 | 15 | 27 | 62 |
| % Molecular weight distribution | 52 | 58 | 50 | 40 | 22 |
| Conjugate molecular weight, kDa | 3,720 | 3,713 | 1,327 | 1,016 | 545 |

The characteristic change of the serotype 9N conjugate was observed by controlling the polysaccharide concentration in the conjugation reaction solution on the basis of the preparation method. The result was summarized in Table 6.

TABLE 6

| Conjugate number | 2-12 | 2-13 | 2-14 | 2-15 | 2-16 |
|---|---|---|---|---|---|
| Activated polysaccharide molecular weight, kDa | | | 560 | | |
| D0 | | | 6.1 | | |
| Input ratio (P:S) | | | 0.8:1 | | |
| Polysaccharide concentration in conjugation reaction solution, g/L | 10.0 | 12.5 | 15.0 | 17.5 | 20.0 |
| % Conjugate yield | 20 | 31 | 28 | 40 | 42 |
| Ratio of saccharides to protein | 1.0 | 1.0 | 0.93 | 0.99 | 0.97 |
| % Free polysaccharide | 32 | 30 | 22 | 21 | 18 |
| % Molecular weight distribution | 17 | 27 | 40 | 47 | 54 |
| Conjugate molecular weight, kDa | 560 | 546 | 845 | 932 | 1,438 |

Research on Immunogenicity of Serotype 9N Polysaccharide-Protein Conjugate

A monovalent conjugate composition comprising a polysaccharide-protein conjugate from *Streptococcus pneumoniae* serotype 9N all individually conjugated to CRM197 was formulated.

The immunogenicity of the monovalent immunogenic composition of the Table 4 to Table 6 was analyzed using ELISA in a rabbit, thereby measuring a serotype-specific IgG concentration in serum.

The female New Zealand white rabbit group was immunized via intramuscular route in the same manner as serotype 2.

The analysis result was shown in Table 7. The rabbit immunized with the monovalent conjugate composition (conjugate number 2-8) exhibited a significant increase of the total IgG titer against serotype 9N. In the rabbit immunized with other conjugate, a significant increase of the total IgG titer was shown.

The values of the following Table 7 are the result of showing the measured IgG concentration after immunizing with the conjugate number 2-8 of the Table 5.

TABLE 7

| | IgG concentration (U/mL) | |
|---|---|---|
| Serotype | Pre-immunization | Post-immunization |
| 9N | 130.0 | 656,345.3 |

[3. *Streptococcus pneumoniae* Serotype 17F-Derived Polysaccharide-Protein Conjugate]

Preparation of *Streptococcus pneumoniae* Serotype 17F-Derived Polysaccharide-Protein Conjugate Preparation of Cell Band for Master and Preparation

*Streptococcus pneumoniae* serotype 17F was obtained from American Type Culture Collection (ATCC) (strain ATCC 6317). In order to enhance the strain and remove components of animal origin, a seed stock was cultured for several generations. It was progressed in the same manner as serotype 2.

Fermentation

It was progressed in the same manner as serotype 2.

Purification

It was progressed in the same manner as serotype 2.

Activation

The final polysaccharide concentration was adjusted so as to be about 2.0 g/L in 0.01N hydrochloric acid solution by adding a calculated amount of 0.1N hydrochloric acid solution and WFI in order. For hydrolysis of the polysaccharide, the hydrolysis reaction was carried out at about 60° C. for 60 minutes. After lowering the temperature of the reaction solution to a room temperature, the reaction pH was adjusted to approximately 6.0 by adding 0.1M sodium monohydrogen phosphate solution. After adjusting the pH, the temperature was adjusted to 23° C. The oxidation was initiated by adding sodium periodic acid of approximately 0.008~0.219 mg per 1 mg sugar. The oxidation reaction was carried out at 23° C. for 18 hours.

The concentration and diafiltration of the activated polysaccharide were performed using 100 kDa MWCO ultrafiltration membrane. Diafiltration was performed on WFI of 10-fold diafiltration volume. Then, the purified activated polysaccharide was stored at 2~8° C. The purified activated polysaccharide was characterized by in particular, (i) polysaccharide concentration by colorimetric determination, (ii) aldehyde concentration by colorimetric determination, (iii) degree of oxidation and (iv) molecular weight by SEC-MALLS.

SEC-MALLS is used for determining the molecular weights of the polysaccharide and polysaccharide-protein conjugate. SEC is used for separating the polysaccharide by fluid dynamical volume. The refractive index (RI) and multi-angle laser light scattering detector are used for molecular weight determination. When light interacts with a material, light is scattering and the amount of scattered light is related to concentration, square of do/dc (unique refractive index increase) and molar mass of a material. The molecular weight measured value is calculated on the basis of the reading value from scattered light signal from MALLS detector and the concentration signal from RI detector.

The degree of oxidation (DO) of the activated polysaccharide was determined by 'mole of sugar repeating unit mole of aldehyde'. By various colorimetry methods, for example, using Anthrone method, the mole of sugar repeating unit was determined. In addition, at the same time, using Park-Johnson colorimetry method, the mole of aldehyde was determined.

Preferably, the activated *Streptococcus pneumoniae* serotype 17F capsular polysaccharide obtained by the method has a degree of oxidation of 1 to 22 and a molecular weight of about 400 kDa to 900 kDa.

Conjugation Process

The activated polysaccharide was combined with the carrier protein, CRM197 at a ratio of CRM197 of 1.0 gram per the activated polysaccharide gram. Subsequently, the combined mixture was lyophilized. Following lyophilization, the lyophilized mixture of the activated polysaccharide and CRM197 was stored at −20° C.

The lyophilized mixture of the activated polysaccharide and CRM197 was recomposed in 0.1M sodium phosphate solution (pH 7.2±0.1). The final polysaccharide concentration in the reaction solution is 15.0 to 25.0 g/L. The conjugation was initiated by adding sodium cyanoborohydride ($NaBH_3CN$) of 1.2 mole equivalent to the mixture, and it was reacted at 37° C. for 48 hours. The conjugation reaction was terminated by adding 0.9% sodium chloride solution at the same volume as the conjugation reaction solution and then adding sodium borohydride ($NaBH_4$) of 2.0 mole equivalent, thereby capping unreacted aldehyde. The capping reaction was conducted at 23° C. for 4.5 hours.

The conjugate solution was diluted with 0.9% sodium chloride solution during the preparation for purification by concentration and diafiltration using 100 kDa MWCO membrane. The diluted conjugate solution was passed through a 0.45 μm filter and purification by concentration and diafiltration was carried out. Diafiltration using 100 kDa MWCO membrane was carried out using 0.9% sodium chloride solution at a 15-fold to 40-fold diafiltration volume. After completing primary diafiltration, the residual solution was filtrated through a 0.2 μm filter and was stored at 2 to 8° C.

The purified serotype 17F conjugate was particularly characterized by (i) polysaccharide concentration by colorimetric determination, (ii) protein concentration by colorimetric determination (Lowry), (iii) ratio of polysaccharides to protein, (iv) molecular size distribution by size exclusion chromatography (CL-4B), (iv) content of free sugar and (v) molecular weight by SEC-MALLS.

The characteristic change of the serotype 17F conjugate was observed by controlling the degree of oxidation (DO) and the polysaccharide concentration in the reaction solution based on the preparation method. The result was summarized in Table 8.

TABLE 8

| Conjugate number | 3-1 | 3-2 | 3-3 | 3-4 | 3-5 | 3-6 | 3-7 | 3-8 | 3-9 |
|---|---|---|---|---|---|---|---|---|---|
| Activated polysaccharide molecular weight, kDa | 551 | 560 | 577 | 628 | | | 801 | | |
| DO | 21.3 | 9.4 | 7.5 | 3.8 | | | 1.3 | | |
| Input ratio (P:S) | | | | | 1:1 | | | | |
| Polysaccharide concentration in conjugation reaction solution, g/L | | 20.0 | | | 15.0 | 17.5 | 20.0 | 22.5 | 25.0 |
| % Conjugate yield | 31 | 48 | 58 | 35 | 28 | 25 | 28 | 37 | 37 |
| Ratio of saccharides to protein | 14.9 | 5.3 | 4.9 | 2.8 | 0.68 | 0.65 | 0.67 | 0.70 | 0.71 |
| % Free polysaccharide | 84 | 82 | 78 | 60 | 8 | 4 | 4 | 6 | 4 |
| % Molecular weight distribution | | | — | | 18 | 38 | 48 | 49 | 58 |
| Conjugate molecular weight, kDa | 372 | 706 | 456 | 1,064 | 1,346 | 2,115 | 2,531 | 3,150 | 4,423 |

Research on Immunogenicity of Serotype 17F Polysaccharide-Protein Conjugate

A monovalent conjugate composition comprising a polysaccharide-protein conjugate from *Streptococcus pneumoniae* serotype 17F all individually conjugated to CRM197 was formulated.

The immunogenicity of the monovalent immunogenic composition of the Table 8 to Table 6 was analyzed using ELISA in a rabbit, thereby measuring a serotype-specific IgG concentration in serum.

The female New Zealand white rabbit group was immunized via intramuscular route in the same manner as serotype 2.

The analysis result was shown in Table 9. The rabbit immunized with the monovalent conjugate composition (conjugate number 3-8) exhibited a significant increase of the total IgG titer against serotype 17F. In the rabbit immunized with other conjugate, a significant increase of the total IgG titer was shown.

The values of the following Table 9 are the result of showing the measured IgG concentration after immunizing with the conjugate number 3-8 of the Table 8.

TABLE 9

| | IgG Concentration (U/mL) | |
|---|---|---|
| Serotype | Pre-immunization | Post-immunization |
| 17F | 130.0 | 227,590.3 |

[4. *Streptococcus pneumoniae* Serotype 20-Derived Polysaccharide-Protein Conjugate]

Preparation of *Streptococcus pneumoniae* Serotype 20-Derived Polysaccharide-Protein Conjugate Preparation of Cell Band for Master and Preparation

*Streptococcus pneumoniae* serotype 20 was obtained from American Type Culture Collection (ATCC) (strain ATCC 6320). It was progressed in the same manner as serotype 2.

Fermentation

It was progressed in the same manner as serotype 2.

Purification

It was progressed in the same manner as serotype 2.

Activation

The final polysaccharide concentration was adjusted so as to be about 2.0 g/L in 0.01N hydrochloric acid solution by adding a calculated amount of 0.1N hydrochloric acid solution and WFI in order. The oxidation was initiated by adding sodium periodic acid of approximately 0.010~0.038 mg per 1 mg sugar. The oxidation reaction was carried out at 23° C. for 18 hours.

The concentration and diafiltration of the activated polysaccharide were performed using 100 kDa MWCO ultrafiltration membrane. Diafiltration was performed on WFI of 10-fold diafiltration volume. Then, the purified activated polysaccharide was stored at 2~8° C. The purified activated polysaccharide was characterized by in particular, (i) polysaccharide concentration by colorimetric determination, (ii)

aldehyde concentration by colorimetric determination, (iii) degree of oxidation and (iv) molecular weight by SEC-MALLS.

SEC-MALLS is used for determining the molecular weights of the polysaccharide and polysaccharide-protein conjugate. SEC is used for separating the polysaccharide by fluid dynamical volume. The refractive index (RI) and multi-angle laser light scattering detector are used for molecular weight determination. When light interacts with a material, light is scattering and the amount of scattered light is related to concentration, square of do/dc (unique refractive index increase) and molar mass of a material. The molecular weight measured value is calculated on the basis of the reading value from scattered light signal from MALLS detector and the concentration signal from RI detector.

The degree of oxidation (DO) of the activated polysaccharide was determined by 'mole of sugar repeating unit÷mole of aldehyde'. By various colorimetry methods, for example, using Anthrone method, the mole of sugar repeating unit was determined. In addition, at the same time, using Park-Johnson colorimetry method, the mole of aldehyde was determined.

Preferably, the activated *Streptococcus pneumoniae* serotype 20 capsular polysaccharide obtained by the method has a degree of oxidation of 4 to 16 and a molecular weight of about 400 kDa to 800 kDa.

Conjugation Process

The activated polysaccharide was combined with the carrier protein, CRM197 at a ratio of CRM197 of 1.0 gram per the activated polysaccharide gram. Subsequently, the combined mixture was lyophilized. Following lyophilization, the lyophilized mixture of the activated polysaccharide and CRM197 was stored at −20° C.

The lyophilized mixture of the activated polysaccharide and CRM197 was recomposed in 0.1M sodium phosphate solution (pH 7.2±0.1). The final polysaccharide concentration in the reaction solution is 15.0 g/L. The conjugation was initiated by adding sodium cyanoborohydride ($NaBH_3CN$) of 1.2 mole equivalent to the mixture, and it was reacted at 37° C. for 48 hours. The conjugation reaction was terminated by adding 0.9% sodium chloride solution at the same volume as the conjugation reaction solution and then adding sodium borohydride ($NaBH_4$) of 2.0 mole equivalent, thereby capping unreacted aldehyde. The capping reaction was conducted at 23° C. for 4.5 hours.

The conjugate solution was diluted with 0.9% sodium chloride solution during the preparation for purification by concentration and diafiltration using 100 kDa MWCO membrane. The diluted conjugate solution was passed through a 0.45 μm filter and 2-step purification by concentration and diafiltration was carried out. Diafiltration using 100 kDa MWCO membrane was carried out using 0.9% sodium chloride solution at a 20-fold diafiltration volume. After completing primary diafiltration, the residual solution was filtrated through a 0.2 μm filter and was stored at 2 to 8° C. The conjugate solution was diluted so as to be less than approximately 0.55 mg/mL concentration and was under sterile filtration, and was stored at 2 to 8° C.

The purified serotype 20 conjugate was particularly characterized by (i) polysaccharide concentration by colorimetric determination, (ii) protein concentration by colorimetric determination (Lowry), (iii) ratio of polysaccharides to protein, (iv) molecular size distribution by size exclusion chromatography (CL-4B), (iv) content of free sugar and (v) molecular weight by SEC-MALLS.

The characteristic change of the serotype 20 conjugate was observed by controlling the degree of oxidation (DO) based on the preparation method. The result was summarized in Table 10.

TABLE 10

| Conjugate number | 4-1 | 4-2 | 4-3 | 4-4 | 4-5 | 4-6 | 4-7 |
|---|---|---|---|---|---|---|---|
| Activated polysaccharide molecular weight, kDa | 651 | 749 | 675 | 463 | 613 | 444 | 712 |
| DO | 15.7 | 15.4 | 8.9 | 7.3 | 6.7 | 4.8 | 4.6 |
| Input ratio (P:S) | | | | 1:1 | | | |
| % Conjugate yield | 65 | 57 | 56 | 49 | 45 | 24 | 20 |
| Ratio of saccharides to protein | 3.7 | 2.9 | 2.5 | 2.7 | 2.2 | 2.1 | 1.5 |
| % Free polysaccharide | 29 | 28 | 16 | 15 | 16 | 11 | 8 |
| % Molecular weight distribution | 84 | — | 79 | 78 | 82 | 78 | — |
| Conjugate molecular weight, kDa | 1,968 | 1,271 | 3,349 | 2,458 | 3,645 | 2,123 | 2,563 |

Research on Immunogenicity of *Streptococcus pneumoniae* Serotype 20 Polysaccharide-Protein Conjugate A monovalent conjugate composition comprising a polysaccharide-protein conjugate from *Streptococcus pneumoniae* serotype 20 all individually conjugated to CRM197 was formulated.

The immunogenicity of the monovalent immunogenic composition of the Table 10 was analyzed using ELISA in a rabbit, thereby measuring a serotype-specific IgG concentration in serum.

The female New Zealand white rabbit group was immunized via intramuscular route in the same manner as serotype 2.

The analysis result was shown in Table 11. The rabbit immunized with the monovalent conjugate composition (conjugate number 4-7) exhibited a significant increase of the total IgG titer against serotype 20. In the rabbit immunized with other conjugate, a significant increase of the total IgG titer was shown.

The values of the following Table 11 is the result of showing the measured IgG concentration after immunizing with the conjugate number 4-7 of the Table 10.

TABLE 11

| | IgG concentration (U/mL) | |
|---|---|---|
| Serotype | Pre-immunization | Post-immunization |
| 20 | 166.2 | 277,210.1 |

EXAMPLE 2. PREPARATION OF MULTIVALENT *STREPTOCOCCUS PNEUMONIAE* POLYSACCHARIDE-PROTEIN CONJUGATE

[5. *Streptococcus pneumoniae* 15-Valent Polysaccharide-Protein Conjugate]

Preparation of *Streptococcus pneumoniae* 15-Valent Polysaccharide-Protein Conjugate A 15-valent conjugate composition comprising the polysaccharide-protein conjugate derived from *Streptococcus pneumoniae* serotypes 1, 2, 3, 4, 5, 6A, 6B, 7F, 9N, 9V, 14, 18C, 19A, 19F, and 23F all individually conjugated to CRM197 (15vPnC) was formulated.

For serotypes 2 and 9N, the conjugate was prepared by the afore-mentioned method, and for other serotypes, the conjugate was prepared according to the method disclosed in Korean Patent Application 2012-0065893.

The required volume of the final bulk concentrate was calculated based on batch volume and bulk saccharide concentration. A required amount of 0.85% sodium chloride, polysorbate 80 and succinate buffer were added to a pre-labeled formulation container, and then the bulk concentrate was added. It was sufficiently mixed and was filtrated through a 0.22 μm filter. During and after addition of bulk aluminum phosphate, the formulated bulk solution was slowly mixed. pH was checked and was adjusted if necessary. The formulated bulk product was stored at 2 to 8° C. The obtained vaccine composition contained each saccharide of 2.2 μg, but 6B of 4.4 μg; CRM 197 carrier protein of about 32 μg; adjuvant of aluminum element of 0.125 mg (0.5 mg aluminum phosphate); sodium chloride about 4.25 mg; succinate buffer about 295 μg; and polysorbate 80 about 100 μg in the total 0.5 mL.

Research on Immunogenicity of *Streptococcus pneumoniae* 15-Valent Polysaccharide-Protein Conjugate IgG Concentration Measurement The immunogenicity of the 15-valent immunogenic composition was analyzed in a rabbit using ELISA, thereby measuring the serotype-specific IgG concentration in serum.

6 female New Zealand white rabbit group of 2.5 kg to 3.5 kg was immunized via intramuscular route at the 0th week with the proposed human clinical dose (conjugate 2.2 μg, except for serotype 6b determined as 4.4 μg; +aluminum 0.25 mg/ml as $AlPO_4$). The rabbit was further immunized at the 3rd week with the same dose of conjugate vaccine, and subsequently blood-gathering was carried out at an interval of 3 weeks. The serotype-specific ELISA was performed in serum samples of each week.

The serotype specific immune response for the vaccine formulation according to the present invention and the vaccine formulation of the comparative example was evaluated by IgG ELISA. The analysis result was summarized in Table 12. It shows IgG concentrations (U/mL) as time passes after inoculation. It was shown that the rabbit immunized by the 15vPnC produced antibodies against serotypes 2 and 9N which could not be obtained with Prevnar13, and particularly, it could induce an equivalent or excellent serum IgG titer compared to Prevnar13, even though the valence number increased by serotype addition.

TABLE 12

| ELISA Type | Prevnar 13 | | | | SK-15 | | | |
|---|---|---|---|---|---|---|---|---|
| | Day 0 | Day 21 | Day 42 | Day 63 | Day 0 | Day 21 | Day 42 | Day 63 |
| 1 | 0 | 8522 | 14187 | 10207 | 0 | 2053 | 17110 | 7752 |
| 2 | — | — | — | — | 134 | 47864 | 36482 | 23790 |
| 3 | 0 | 968 | 7229 | 5330 | 0 | 2084 | 11069 | 10947 |
| 4 | 0 | 3831 | 23100 | 16654 | 0 | 2592 | 15000 | 10179 |
| 5 | 97 | 5597 | 13083 | 14819 | 111 | 4866 | 19615 | 16062 |
| 6A | 0 | 15810 | 28609 | 20581 | 0 | 3634 | 20313 | 10141 |
| 6B | 0 | 12920 | 43575 | 34932 | 0 | 4296 | 29763 | 14204 |
| 7F | 0 | 48129 | 26694 | 18014 | 0 | 43979 | 21590 | 10878 |
| 9N | — | — | — | — | 0 | 9197 | 17085 | 13021 |
| 9V | 436 | 17281 | 35392 | 9442 | 373 | 15128 | 12143 | 12304 |
| 14 | 194 | 8365 | 10403 | 10786 | 416 | 7066 | 13160 | 16043 |
| 18C | 0 | 19101 | 23989 | 24862 | 0 | 19385 | 14192 | 14565 |
| 19A | 0 | 71160 | 136042 | 139273 | 0 | 24713 | 64138 | 59135 |
| 19F | 0 | 40695 | 53165 | 56443 | 0 | 8382 | 38304 | 30852 |
| 23F | 0 | 11171 | 62331 | 47522 | 0 | 7116 | 65352 | 67085 |

OPA Analysis Result

In order to confirm whether the 15-valent polysaccharide-protein conjugate induced a functional antibody reaction, multiplexed opsonophagocytic killing assay (MOPA) was carried out.

By collecting the same amount of serum by each subject, serum was pooled between the same groups. *Streptococcus pneumoniae* was cultured in a THY medium by each serum and was diluted to be 1000 CFU/10 uL. Opsonization buffer 200 uL, diluted serum 10 uL, and diluted *Streptococcus pneumoniae* 10 uL were mixed and it was reacted at a room temperature for 1 hour. The mixed solution of a pre-differentiated HL-60 cell and a complement was added and it was reacted in a $CO_2$ incubator (37° C.) for 1 hour. The phagocytosis was stopped by lowering the temperature and the reaction solution 5 uL was painted out in an agar medium dried for 30 to 60 minutes in advance. It was cultured in the $CO_2$ incubator (37° C.) for 12 to 18 hours and the number of colonies was counted. The OPA titer was represented by the dilution rate in which 50% death was observed. As a comparative example, a 13-valent vaccine (Prevnar13, Pfizer) was used to evaluate in the same manner, and the result was summarized in Table 13.

TABLE 13

| OPA Type | Prevnar 13 | | | SK-15 | | |
|---|---|---|---|---|---|---|
| | Day 21 | Day 42 | Day 63 | Day 21 | Day 42 | Day 63 |
| 1 | 16 | 64 | 64 | 4 | 64 | 64 |
| 2 | — | — | — | 128 | 512 | 512 |
| 3 | 1 | 2 | 4 | 1 | 4 | 4 |
| 4 | 128 | 1024 | 1024 | 128 | 1024 | 1024 |
| 5 | 64 | 256 | 512 | 32 | 256 | 512 |
| 6A | 512 | 2048 | 2048 | 256 | 2048 | 2048 |
| 6B | 256 | 2048 | 2048 | 128 | 2048 | 2048 |
| 7F | 1024 | 2048 | 2048 | 1024 | 2048 | 2048 |
| 9N | — | — | — | 512 | 2048 | 2048 |
| 9V | 256 | 512 | 512 | 256 | 512 | 512 |
| 14 | 256 | 1024 | 1024 | 256 | 1024 | 1024 |
| 18C | 1024 | 1024 | 2048 | 1024 | 512 | 2048 |
| 19A | 512 | 1024 | 2048 | 256 | 1024 | 1024 |
| 19F | 256 | 1024 | 1024 | 128 | 512 | 512 |
| 23F | 256 | 2048 | 2048 | 256 | 2048 | 2048 |

[6. *Streptococcus pneumoniae* 23-Valent Polysaccharide-Protein Conjugate]

Preparation of *Streptococcus pneumoniae* 23-Valent Polysaccharide-Protein Conjugate A 23-valent conjugate composition comprising the polysaccharide-protein conjugate in which polysaccharides derived from *Streptococcus pneumoniae* serotypes 1, 2, 6A, 6B, 7F, 8, 9N, 9V, 10A, 11A, 12F, 14, 15B, 17F, 18C, 19A, 19F, 20, 22F, 23F and 33F were conjugated to CRM197 and the polysaccharide-protein conjugate in which *Streptococcus pneumoniae* serotypes 3 and 5 were conjugated to TT (Tenus toxoid) (23vPnC) was formulated.

For serotypes 2, 9N, 17F and 20, the conjugate was prepared by the afore-mentioned method, and for other serotypes, the conjugate conjugated to CRM197 or TT was prepared according to the methods disclosed in Korean Patent Application 2012-0065893, U.S. Patent Applications 62/371,529, 62/371,553 and 62/626,482.

The required volume of the final bulk concentrate was calculated based on batch volume and bulk saccharide concentration. A required amount of 0.85% sodium chloride, polysorbate 80 and succinate buffer were added to a pre-labeled formulation container, and then the bulk concentrate was added. It was sufficiently mixed and was filtrated through a 0.22 μm filter. During and after addition of bulk aluminum phosphate, the formulated bulk solution was slowly mixed. pH was checked and was adjusted if necessary. The formulated bulk product was stored at 2 to 8° C. The obtained vaccine composition contained each saccharide of 2.2 μg, but 6B of 4.4 μg; CRM 197 carrier protein of about 50 to 85 μg; an experimental amount of aluminum adjuvant (for example, in case of Group 4 in Table 14, aluminum element of 0.125 mg, that is, 0.5 mg aluminum phosphate); sodium chloride about 4.25 mg; succinate buffer about 295 μg; and polysorbate 80 about 100 μg in the total 0.5 mL.

gathering was carried out at the 4th week. The serotype-specific ELISA was performed in the 0th and 4th serum samples.

As a comparative example, a 13-valent vaccine (Prevnar13, Pfizer) was used to evaluate in the same manner, and the analysis result was summarized in Table 14. It shows IgG concentrations (U/mL) as 4th week passes after inoculation.

The geometric mean titer (GMT) measured in the pooled serum sample after administering the 23vPnV vaccine and Prevnar13 twice was proposed. These data demonstrate that a higher level of IgG antibody is induced compared to the same vaccine which does not contain an adjuvant, when an adjuvant is comprised in the 23vPnV formulation. In particular, it was confirmed that a 23-valent immunogenic vaccine comprising all serotypes 2, 9N, 17F and 20 could be obtained. As could be seen in the following result, in particular, an antibody against serotype 2 and the like, which could not be obtained by Prevnar13, could be produced. In addition, it was confirmed that it could induce an immune response against all the comprised serotype without greatly affecting production of an antibody against an antigen of other serotypes, despite greatly increased valence number.

TABLE 14

|  | Group 1: PCV24 I alum 0 Control group | Group 2: PCV24 I alum 62.5 | Group 3: PCV24 I alum 125 | Group 4: PCV24 I alum 250 | Group 5: PCV24 I alum 500 | Group 6: PCV24 I alum 1000 | Group 7 (Prevnar ® 13) Reference group |
|---|---|---|---|---|---|---|---|
| Type 1 | 4421 | 10951 | 11205 | 9595 | 12821.5 | 12038.5 | 9131.0 |
| Type 2 | 4850.7 | 7347 | 7358.2 | 6833.1 | 9909.4 | 7875.3 | — |
| Type 3 | 15552.6 | 17362.7 | 23574.8 | 11718 | 24425.5 | 18313.2 | 4265.9 |
| Type 5 | 5676.1 | 11391.8 | 10274.5 | 10699.7 | 13622.7 | 15469 | 5930.1 |
| Type 6A | 15265.3 | 13034.2 | 30631.9 | 17203.6 | 21335.1 | 21011.1 | 5697.2 |
| Type 6B | 3566.3 | 8567.3 | 17964.5 | 8101.7 | 21985.6 | 19993.7 | 4136.6 |
| Type 7F | 10474.8 | 32904.5 | 36935.5 | 28650.3 | 45878.8 | 48559 | 31991.5 |
| Type 8 | 18684.5 | 26486.5 | 39449.2 | 26369.3 | 43372.9 | 56812.6 | — |
| Type 9N | 29350.5 | 52915.1 | 61918.7 | 25465.9 | 73406.3 | 95465.2 | — |
| Type 9V | 9041 | 19108 | 24479.9 | 24602.9 | 30087.5 | 36732.8 | 23053.6 |
| Type 10A | 19833.3 | 38644.7 | 39959.5 | 73948.6 | 40524.8 | 60464.4 | — |
| Type 11A | 893.6 | 3845.9 | 4447.6 | 2474.3 | 5683.2 | 8358.5 | — |
| Type 12F | 4785.2 | 10497.8 | 7381.7 | 8444.8 | 8113.6 | 14211.8 | — |
| Type 14 | 9177.7 | 17574 | 12811.4 | 15834.6 | 13543.4 | 23876.5 | 11178.8 |
| Type 15B | 4908.7 | 17293.7 | 18345.2 | 4936.3 | 19436.1 | 28797.9 | — |
| Type 17F | 7441.1 | 9373.4 | 14848.8 | 10186.3 | 14319.7 | 32906.8 | — |
| Type 18C | 16747.2 | 27864.6 | 44605.6 | 29416.3 | 37658 | 38860.5 | 34163.2 |
| Type 19A | 781.9 | 4088.9 | 5846.5 | 4114.6 | 8824.5 | 12216.5 | 14381.8 |
| Type 19F | 4501.9 | 32543.6 | 27502.3 | 28629.2 | 36290.5 | 68218.5 | 15315.5 |
| Type 20 | 18252.8 | 32553.5 | 34663.5 | 21760.3 | 37978.2 | 44630 | — |
| Type 22F | 6790.8 | 24687.1 | 24800.1 | 19953 | 42634.5 | 55543.4 | — |
| Type 23F | 823.6 | 3859.8 | 7938 | 6634 | 9468.7 | 10348.8 | 9440.5 |
| Type 33F | 7261.6 | 23864.8 | 24843.6 | 20105.5 | 22586.9 | 28958 | — |

Research on Immunogenicity of *Streptococcus pneumoniae* 23-Valent Polysaccharide-Protein Conjugate IgG Concentration Measurement The immunogenicity of the 23-valent immunogenic composition was analyzed in a rabbit using ELISA, thereby measuring the serotype-specific IgG concentration in serum. The ability of inducing a serotype-specific immune response of the 23vPnC vaccine containing an adjuvant was investigated.

5 female New Zealand white rabbit group of 2.5 kg to 3.5 kg was immunized via intramuscular route at the 0th week with the proposed human clinical dose (conjugate 2.2 μg, except for serotype 6b determined as 4.4 μg) in which aluminum of 0.0625 mg/ml, 0.125 mg/ml, 0.25 mg/ml, 0.5 mg/ml and 1 mg/ml, respectively was comprised as AlPO4. The rabbit was further immunized at the 2nd week with the same dose of conjugate vaccine, and subsequently blood-

[7. *Streptococcus pneumoniae* 24-Valent Polysaccharide-Protein Conjugate]

Preparation of *Streptococcus pneumoniae* 24-Valent Polysaccharide-Protein Conjugate A 24-valent conjugate composition comprising the polysaccharide-protein conjugate in which polysaccharides derived from *Streptococcus pneumoniae* serotypes 2, 3, 4, 6A, 6B, 7F, 8, 9N, 9V, 10A, 11A, 12F, 14, 15B, 17F, 18C, 19A, 19F, 20, 22F, 23F and 33F were conjugated to CRM197 and the polysaccharide-protein conjugate in which *Streptococcus pneumoniae* serotypes 1 and 5 were conjugated to TT (Tenus toxoid) (24vPnC) was formulated. For serotypes 2, 9N, 17F and 20, the conjugate was prepared by the afore-mentioned method, and for other serotypes, the conjugate conjugated to CRM197 or TT was prepared according to the methods disclosed in Korean Patent Application 2012-0065893, U.S. Patent Applications 62/371,529, 62/371,553 and 62/626,482.

The required volume of the final bulk concentrate was calculated based on batch volume and bulk saccharide concentration. A required amount of 0.85% sodium chloride, polysorbate 80 and succinate buffer were added to a pre-labeled formulation container, and then the bulk concentrate was added. It was sufficiently mixed and was filtrated through a 0.22 μm filter. During and after addition of bulk aluminum phosphate, the formulated bulk solution was slowly mixed. pH was checked and was adjusted if necessary. The formulated bulk product was stored at 2 to 8° C. The obtained vaccine composition contained each saccharide of 2.2 μg, but 6B of 4.4 μg; CRM 197 carrier protein of about 50 to 90 μg; adjuvant of aluminum element of 0.125 mg (0.5 mg aluminum phosphate); sodium chloride about 4.25 mg; succinate buffer about 295 μg; and polysorbate 80 about 100 μg in the total 0.5 mL.

Research on Immunogenicity of *Streptococcus pneumoniae* 24-Valent Polysaccharide-Protein Conjugate OPA Analysis Result In order to confirm whether the 24-valent polysaccharide-protein conjugate induced a functional antibody reaction, opsonophagocytic killing assay (OPA) was carried out in three rabbits in the same manner as the 15-valent vaccine.

TABLE 15

| Serotype | PCV24 | Prevnar 13 |
|---|---|---|
| 1 | 309 | 54 |
| 2 | 490 | — |
| 3 | 407 | 393 |
| 4 | 1290 | 2072 |
| 5 | 1516 | 306 |
| 6A | 1817 | 2355 |
| 6B | 2888 | 1614 |
| 7F | 1277 | 952 |
| 8 | 279 | — |
| 9N | 653 | 52 |
| 9V | 178 | 324 |
| 10A | 658 | — |
| 11A | 675 | — |
| 12F | 471 | — |
| 14 | 959 | 539 |
| 15B | 371 | — |
| 17F | 348 | — |
| 18C | 1357 | 1996 |
| 19A | 642 | 1870 |
| 19F | 1521 | 1516 |
| 20 | 306 | — |
| 22F | 1703 | — |
| 23F | 1531 | 928 |
| 33F | 428 | — |

Through the result, it was confirmed that a 24-valent vaccine comprising all the serotypes 2, 9N, 17F and 20 could be obtained. As could be seen in the result, in particular, an antibody against serotypes 2, 17F and the like, which could not be obtained by Prevnar13, could be produced. In addition, it was confirmed that the immune response against all comprised serotypes could be induced without greatly affecting production of an antibody against an antigen of other serotypes, although 11 serotypes were added to Prevnar13.

INDUSTRIAL APPLICABILITY

The immunogenic composition of one example of the present invention may be used as medicament.

The immunogenic composition of one example of the present invention may be used as various therapeutic or prophylactic methods for prevention, treatment or improvement of bacterial infection, diseases or conditions. In particular, the immunogenic composition disclosed in the present invention may be used for prevention, treatment or improvement of *Streptococcus pneumoniae* infection, diseases or conditions in a subject.

In one embodiment, a method for inducing an immune response against *Streptococcus pneumoniae* in a subject, comprising administering an effective dose of the immunogenic composition of the present invention into the subject may be provided.

The invention claimed is:

1. An immunogenic composition comprising 24 different *Streptococcus pneumoniae* capsular polysaccharide-protein conjugates,
wherein each capsular polysaccharide-protein conjugate comprises a carrier protein conjugated to a capsular polysaccharide derived from a different serotype of *Streptococcus pneumoniae*, wherein the *Streptococcus pneumoniae* serotypes are selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F; and
wherein the capsular polysaccharides from serotypes 1 and 5 are conjugated to tetanus toxoid and the capsular polysaccharides from serotypes 2, 3, 4, 6A, 6B, 7F, 8, 9N, 9V, 10A, 11A, 12F, 14, 15B, 17F, 18C, 19A, 19F, 20, 22F, 23F, and 33F are conjugated to $CRM_{197}$,
wherein the capsular polysaccharide from serotype 2 has a molecular weight of 100 to 400 kDa and a degree of oxidation of 2 to 18,
wherein the capsular polysaccharide from serotype 9N has a molecular weight of 200 to 700 kDa and a degree of oxidation of 2 to 19,
wherein the capsular polysaccharide from serotype 17F has a molecular weight of 400 to 900 kDa and a degree of oxidation of 1 to 22, and
wherein the capsular polysaccharide from serotype 20 has a molecular weight of 400 to 800 kDa and a degree of oxidation of 4 to 16.

2. The immunogenic composition of claim 1, wherein:
the capsular polysaccharide-protein conjugate comprising the capsular polysaccharide from serotype 2 has a molecular weight of 1,000 to 16,000 kDa, or
the capsular polysaccharide-protein conjugate comprising the capsular polysaccharide from serotype 20 has a molecular weight of 1,000 to 4,000 kDa.

3. The immunogenic composition of claim 1, wherein:
the weight ratio of the capsular polysaccharide from serotype 2 to the carrier protein is 0.5 to 2.0, or
the weight ratio of the capsular polysaccharide from serotype 17F to the carrier protein is 0.5 to 18, or
the weight ratio of the capsular polysaccharide from serotype 20 to the carrier protein is 1 to 5.

4. The immunogenic composition of claim 1, wherein:
20 to 60% of the total molecular weight of the capsular polysaccharide-protein conjugate comprising the capsular polysaccharide from serotype 2 is present within 0.3 Kd in a 4% Cross-linked Agarose beads (CL-4B) column, or
15 to 60% of the total molecular weight of the capsular polysaccharide-protein conjugate comprising the capsular polysaccharide from serotype 17F is present within 0.3 Kd in a CL-4B column, or
70 to 90% of the total molecular weight of the capsular polysaccharide-protein conjugate comprising the capsular polysaccharide from serotype 20 is present within 0.3 Kd in a CL-4B column.

5. The immunogenic composition of claim 1, wherein the immunogenic composition comprises a physiologically acceptable vehicle.

6. A vaccine comprising the immunogenic composition of claim 1 and a pharmaceutically acceptable excipient, carrier or diluent.

7. A method of preparing the immunogenic composition of claim 1, the method comprising:
(a) fermenting and dissolving bacterial cells which produce capsular polysaccharides derived from *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F, and 33F;
(b) purifying the capsular polysaccharides from the dissolved bacterial cells;
(c) activating the capsular polysaccharides with an oxidizing agent; and
(d) combining each of the capsular polysaccharides with a carrier protein to form a *Streptococcus pneumoniae* capsular polysaccharide-protein conjugate,
wherein the capsular polysaccharides from serotypes 1 and 5 are conjugated to tetanus toxoid and the capsular polysaccharides from serotypes 2, 3, 4, 6A, 6B, 7F, 8, 9N, 9V, 10A, 11A, 12F, 14, 15B, 17F, 18C, 19A, 19F, 20, 22F, 23F, and 33F are conjugated to $CRM_{197}$,
wherein the capsular polysaccharide from serotype 2 has a molecular weight of 100 to 400 kDa and a degree of oxidation of 2 to 18,
wherein the capsular polysaccharide from serotype 9N has a molecular weight of 200 to 700 kDa and a degree of oxidation of 2 to 19,
wherein the capsular polysaccharide from serotype 17F has a molecular weight of 400 to 900 kDa and a degree of oxidation of 1 to 22, and
wherein the capsular polysaccharide from serotype 20 has a molecular weight of 400 to 800 kDa and a degree of oxidation of 4 to 16.

8. The method of claim 7, wherein the method further comprises hydrolyzing the capsular polysaccharide to size it, before step (c), in case of the capsular polysaccharides derived from serotypes 2 and 17F.

9. The method of claim 7, wherein the *Streptococcus pneumoniae* capsular polysaccharide-protein conjugate is formed by reacting with one or more reducing agents selected from the group consisting of cyanoborohydride, borane-pyridine and borohydride exchange resin.

10. The method of claim 7, wherein the activating step (c) comprises reacting 0.01-0.22 μg of periodate per 1 μg capsular polysaccharide at a temperature of 20 to 25° C. for 15 to 20 hours.

11. A method for preventing or treating, a disease or condition caused by *Streptococcus pneumoniae* in a subject, the method comprising administering the immunogenic composition of claim 1 to the subject.

12. The method of claim 11, wherein the disease or condition caused by *Streptococcus pneumoniae* is pneumonia, sinusitis, otitis media, acute otitis media, cerebromeningitis, bacteriemia, septicemia, pyothorax, conjunctivitis, osteomyelitis, septic arthritis, endocarditis, peritonitis, pericarditis, mastoiditis, cellulitis, soft tissue infection, or brain abscess.

13. A method of inducing an immune response against *Streptococcus pneumoniae* in a subject, the method comprising administering the immunogenic composition of claim 1 to the subject.

14. A method for preventing or treating a disease or condition caused by *Streptococcus pneumoniae* in a subject, the method comprising administering the vaccine of claim 6 to the subject.

15. The method of claim 14, wherein the disease or condition caused by *Streptococcus pneumoniae* is pneumonia, sinusitis, otitis media, acute otitis media, cerebromeningitis, bacteriemia, septicemia, pyothorax, conjunctivitis, osteomyelitis, septic arthritis, endocarditis, peritonitis, pericarditis, mastoiditis, cellulitis, soft tissue infection, or brain abscess.

16. A method of inducing an immune response against *Streptococcus pneumoniae* in a subject, the method comprising administering the vaccine of claim 6 to the subject.

* * * * *

UNITED STATES PATENT AND TRADEMARK OFFICE
CERTIFICATE OF CORRECTION

PATENT NO. : 11,951,162 B2
APPLICATION NO. : 17/047563
DATED : April 9, 2024
INVENTOR(S) : Hun Kim et al.

Page 1 of 1

It is certified that error appears in the above-identified patent and that said Letters Patent is hereby corrected as shown below:

In the Claims

Column 47, Lines 14-15, Claim 7, "the dissolved bacterial cells" should be --the bacterial cells--;

Column 48, Line 8, Claim 10, "C." should be --C--;

Column 48, Line 10, Claim 11, "treating," should be --treating--.

Signed and Sealed this
Twenty-third Day of July, 2024

Katherine Kelly Vidal
*Director of the United States Patent and Trademark Office*